(12) United States Patent
Jessberger et al.

(10) Patent No.: US 9,422,568 B2
(45) Date of Patent: Aug. 23, 2016

(54) PROCESS FOR PREPARING L-AMINO ACIDS

(71) Applicants: Nadja Jessberger, Herzogenaurach (DE); Andreas Burkovski, Erlangen (DE); Brigitte Bathe, Salzkotten (DE); Alexander Reth, Bielefeld (DE)

(72) Inventors: Nadja Jessberger, Herzogenaurach (DE); Andreas Burkovski, Erlangen (DE); Brigitte Bathe, Salzkotten (DE); Alexander Reth, Bielefeld (DE)

(73) Assignee: EVONIK DEGUSSA GmbH, Essen (DE)

( * ) Notice: Subject to any disclaimer, the term of this patent is extended or adjusted under 35 U.S.C. 154(b) by 0 days.

(21) Appl. No.: 14/059,900

(22) Filed: Oct. 22, 2013

(65) Prior Publication Data

US 2014/0127787 A1  May 8, 2014

Related U.S. Application Data

(62) Division of application No. 12/468,512, filed on May 19, 2009, now Pat. No. 8,697,850.

(60) Provisional application No. 61/147,271, filed on Jan. 26, 2009.

(30) Foreign Application Priority Data

May 20, 2008  (DE) .......................... 10 2008 001 874

(51) Int. Cl.
| | |
|---|---|
| *C12N 1/20* | (2006.01) |
| *C12N 15/00* | (2006.01) |
| *C07H 21/04* | (2006.01) |
| *C12N 15/77* | (2006.01) |
| *C07K 14/34* | (2006.01) |
| *C12P 13/04* | (2006.01) |
| *C12P 13/08* | (2006.01) |

(52) U.S. Cl.
CPC ................ *C12N 15/77* (2013.01); *C07K 14/34* (2013.01); *C12P 13/04* (2013.01); *C12P 13/08* (2013.01)

(58) Field of Classification Search
None
See application file for complete search history.

(56) References Cited

U.S. PATENT DOCUMENTS

| | | | |
|---|---|---|---|
| 6,921,651 B2 | 7/2005 | Farwick et al. | |
| 7,049,106 B2 | 5/2006 | Farwick et al. | |
| 7,144,724 B2 | 12/2006 | Farwick et al. | |
| 8,133,714 B2 | 3/2012 | Bathe et al. | |
| 2005/0014236 A1* | 1/2005 | Matsuzaki .............. | C12P 13/10 435/115 |
| 2007/0042474 A1 | 2/2007 | Pompejus et al. | |
| 2012/0214211 A1 | 8/2012 | Bathe et al. | |

FOREIGN PATENT DOCUMENTS

EP           1 460 128 A1     9/2004

OTHER PUBLICATIONS

Gabriele Beckers, et al. "Regulation of AmtR-Controlled Gene Expression in Corynebacterium Glutamicum: Mechanism and Characterization of the AmtR Regulon", Molecular Microbiology, vol. 58, No. 2, XP002539889, Oct. 2005, pp. 580-595.
Whisstock et al. Quaterly Reviews of Biophysics, 2003, "Prediction of protein function from protein sequence and structure", 36(3):307-340.
Witkowski et al. Conversion of a beta-ketoacyl synthase to a malonyl decarboxylase by replacement of the active-site cysteine with glutamine, Biochemistry. Sep. 7, 1999;38(36):11643-50.
Yukawa, et al. Comparative analysis of the Corynebacterium glutamicum group and complete genome sequence of strain R, Microbiology, Apr. 2007, vol. 153, No. 4, 1042-1058.

\* cited by examiner

*Primary Examiner* — Iqbal H Chowdhury
(74) *Attorney, Agent, or Firm* — Oblon, McClelland, Maier & Neustadt, L.L.P.

(57) ABSTRACT

A process for preparing L-amino acids employing coryneform bacteria in which the AmtR regulator has been attenuated is provided. Recombinant bacteria, polynucleotides and vectors corresponding to or having the attenuated AmtR regulator are disclosed.

12 Claims, No Drawings

PROCESS FOR PREPARING L-AMINO ACIDS

CROSS-REFERENCE TO RELATED APPLICATIONS

This application claims priority to U.S. Ser. No. 12/468,512 filed May 19, 2009, which claims priority to U.S. Provisional Application No. 61/147,271, filed Jan. 26, 2009, and German Application No. 102008001874.0 filed May 20, 2008, the disclosures of which are incorporated herein by reference in their entireties.

BACKGROUND OF THE INVENTION

1. Field of the Invention

The invention relates to a process for preparing L-amino acids comprising a recombinant coryneform bacteria in which the AmtR regulator has been attenuated.

2. Discussion of the Background

L-Amino acids are used in human medicine, in the pharmaceutical industry, in the food industry and very particularly in livestock nutrition.

It is known that L-amino acids such as, for example, L-lysine are prepared by fermentation of strains of coryneform bacteria, especially *Corynebacterium glutamicum*. Because of their great importance, work to improve the methods used to prepare L-amino acids has been continuous. Process improvements may relate to fermentation technology measures such as, for example, stirring and supplying oxygen, or to the composition of the nutrient media, such as, for example, the sugar concentration during fermentation, or to the working up to product form by, for example ion exchange chromatography, or to the intrinsic output properties of the microorganism itself.

The methods used for improving the output properties of these microorganisms include mutagenesis, followed by selection and choice of mutants. The strains obtained in this way are resistant to antimetabolites or are auxotrophic for metabolites of regulatory importance, and produce L-amino acids. A known antimetabolite is the lysine analogue S-(2-aminoethyl)-L-cysteine (AEC).

Methods of recombinant DNA technology have likewise been used for strain improvement of L-amino acid-producing strains of the genus *Corynebacterium*, especially *Corynebacterium glutamicum*. These methods have been directed to modifying individual amino acid biosynthesis genes and investigating the effect on amino acid production.

Reference sources describing the biology, genetics and biotechnology of *Corynebacterium glutamicum* include in the "Handbook of *Corynebacterium glutamicum*" (Eds.: L. Eggeling and M. Bott, CRC Press, Taylor & Francis, 2005), the special edition of the Journal of Biotechnology (Chief Editor: A. Pühler) entitled "A New Era in *Corynebacterium glutamicum* Biotechnology" (Journal of Biotechnology 104/1-3, (2003)) and the book by T. Scheper (Managing Editor) "Microbial Production of L-Amino Acids" (Advances in Biochemical Engineering/Biotechnology 79, Springer Verlag, Berlin, Germany, 2003).

The nucleotide sequence of the genome of *Corynebacterium glutamicum* ATCC13032 is described by Ikeda and Nakagawa (Applied Microbiology and Biotechnology 62, 99-109 (2003)), in EP 1 108 790 and by Kalinowski et al. (Journal of Biotechnology 104(1-3), (2003)). The nucleotide sequence of the genome of *Corynebacterium glutamicum* R is described by Yukawa et al. (Microbiology 153(4):1042-1058 (2007)).

The nucleotide sequence of the genome of *Corynebacterium efficiens* is described by Nishio et al. (Genome Research. 13 (7), 1572-1579 (2003)).

The nucleotide sequences of the genome of *Corynebacterium glutamicum* and *Corynebacterium efficiens* are likewise available in the database of the National Center for Biotechnology Information (NCBI) of the National Library of Medicine (Bethesda, Md., USA), in the DNA Data Bank of Japan (DDBJ, Mishima, Japan) or in the nucleotide sequence database of the European Molecular Biologies Laboratories (EMBL, Heidelberg, Germany or Cambridge, UK).

The structural definition of the *Corynebacterium glutamicum* genome made it possible inter alia to carry out wide-ranging investigations on the metabolism and regulatory network of this bacterium (Silberbach and Burkovski, Journal of Biotechnology 126(1): 101-110 (2006)).

An essential precondition for synthesizing amino acids and in general for growing the cells is an appropriate supply of nitrogen. *C. glutamicum* is able to utilize various nitrogen sources, including ammonium, L-glutamic acid, glutamine and urea. Depending on the concentration and nature of the available nitrogen source, particular enzymes and transport systems are synthesized and activated. For energy reasons, strict regulation is necessary ("nitrogen control"). The regulation of gene expression and the global signal transduction in the nitrogen metabolism of *C. glutamicum* has been investigated in detail by various authors.

The expression of nitrogen-regulated genes is regulated in *C. glutamicum* by the global repressor AmtR. When the nitrogen supply is good, AmtR represses expression of the genes of the amt-soxA-ocd operon, of the gltBD operon, of the amtB-glnK-glnD operon and of glnA and crnT genes (Jacoby et al., Molecular Microbiology 37: 964-977 (2000); Beckers et al., Microbiology, 147: 2961-2170 (2001); Nolden et al., FEMS Microbiological Letters 201: 91-98 (2001)). It was possible in further investigations (Beckers et al., Journal of Bacteriology 186(22): 7645-52 (2004); Beckers et al., Molecular Microbiology 58(2): 580-595 (2005)) inter alia to show an AmtR-dependent regulation also for the genes of the gluABCD operon, of the NCgl1915-1918 operon, of the urtABCDE operon, of the ureABCEFGD operon, and the codA gene and the NCgl1099 gene.

EP 1 460 128 reports on the effect of deleting the amtR gene in a ΔargR strain on the production of various amino acids.

OBJECT OF THE INVENTION

Even after all the work described, a need to improve methods of L-amino acid production, in terms of efficiency, yield and purity remains. This and other objects have been achieved by the present invention, the first embodiment of which includes: a recombinant, L-amino acid-secreting, coryneform bacterium comprising an amtR gene which codes for an AmtR regulator wherein an amino acid sequence of the amtR gene is at least 90% identical to the amino acid sequence of SEQ ID NO:2 and length of amino acids of the amtR gene essentially comprises 222 amino acids, and the amtR gene is attenuated by at least one of the measures selected from the group consisting of a) replacement of the nucleobase guanine at position 7 of the promoter region of the amtR gene shown in SEQ ID NO:5 by thymine, b) replacement of the nucleobase cytosine at position 11 of the promoter region of the amtR gene shown in SEQ ID NO:5 by guanine, c) replacement of the nucleobase thymine at position 40 of the promoter region of the amtR gene shown in SEQ ID NO:5 by guanine, d) replacement of the nucleobase thymine at position 45 of the promoter region of the amtR gene shown in SEQ ID NO:5 by guanine, e) deletion of one or more of the nucleobases of position 40 to 45, preferably deletion of all nucleobases of position 40 to 45, of the promoter region of the amtR gene shown in SEQ ID NO:5, f) deletion of one or more of the nucleobases between position 72 and 78 of the promoter region of the amtR gene shown in SEQ ID NO:5, g) replacement of one or more of the nucleobases adenine or guanine between position 72 and 78 of the promoter region of the amtR gene shown in SEQ ID NO:5 by thymine or cytosine, h) exchange of the ATG start codon at position 1 to 3 of the coding region of the amtR gene for a GTG or TTG start codon, i) exchange of the glycine at position 3 of the amino acid sequence of SEQ ID NO:2 for another proteinogenic L-amino acid, j) exchange of the L-isoleucine at position 24 of the amino acid sequence of SEQ ID NO:2 for an amino acid selected from the group of L-asparagine, L-glutamine, L-glutamic acid and L-aspartic acid, preferably L-aspartic acid, k) exchange of the L-leucine at position 31 of the amino acid sequence of SEQ ID NO:2 for an amino acid selected from the group of L-proline, L-asparagine, L-glutamine, L-phenylalanine, L-tyrosine, L-tryptophan, L-glutamic acid and L-aspartic acid, preferably L-proline, l) exchange of the L-phenylalanine at position 32 of the amino acid sequence of SEQ ID NO:2 for an amino acid selected from the group of glycine, L-glutamic acid, L-aspartic acid, L-proline and L-cysteine, preferably L-proline, m) exchange of the glycine at position 36 of the amino acid sequence of SEQ ID NO:2 for an amino acid selected from the group of L-glutamic acid, L-aspartic acid, L-isoleucine, L-histidine and L-phenylalanine, preferably L-histidine, L-glutamic acid or L-aspartic acid, n) exchange of the L-threonine at position 42 of the amino acid sequence of SEQ ID NO:2 for an amino acid selected from the group of L-proline, L-isoleucine, L-methionine, L-glutamine, L-tryptophan, L-glutamic acid and L-aspartic acid, preferably L-glutamic acid, o) exchange of the glycine at position 50 of the amino acid sequence of SEQ ID NO:2 for an amino acid selected from the group of L-glutamic acid, L-aspartic acid, L-isoleucine, L-histidine, L-tryptophan and L-phenylalanine, preferably L-tryptophan, p) exchange of the L-glutamine at position 53 of the amino acid sequence of SEQ ID NO:2 for an amino acid selected from the group of L-cysteine, L-methionine, L-tyrosine, L-tryptophan and L-phenylalanine, preferably L-phenylalanine, q) exchange of the L-alanine at position 54 of the amino acid sequence of SEQ ID NO:2 for an amino acid selected from the group of L-phenylalanine, L-isoleucine, L-tryptophan, L-tyrosine, L-histidine, L-glutamic acid and L-aspartic acid, preferably L-histidine, r) exchange of the L-serine at position 55 of the amino acid sequence of SEQ ID NO:2 for an amino acid selected from the group of L-proline, L-phenylalanine, L-tryptophan, L-lysine, L-arginine, L-glutamic acid and L-aspartic acid, preferably L-phenylalanine, s) exchange of the L-tyrosine at position 57 of the amino acid sequence of SEQ ID NO:2 for an amino acid selected from the group of L-proline, glycine, L-methionine, L-glutamic acid and L-aspartic acid, preferably L-aspartic acid, t) exchange of the L-tyrosine at position 58 of the amino acid sequence of SEQ ID NO:2 for an amino acid selected from the group of L-proline, L-methionine and L-cysteine, preferably L-proline, u) exchange of the L-histidine at position 59 of the amino acid sequence of SEQ ID NO:2 for an amino acid selected from the group of L-lysine, L-aspartic acid, L-isoleucine, L-proline and glycine, preferably L-proline, and v) exchange of the L-lysine at position 63 of the amino acid sequence of SEQ ID NO:2 for an amino acid selected from the group of L-alanine, L-glutamic acid, L-aspartic acid, L-asparagine, L-tyrosine and L-tryptophan, preferably L-asparagine.

a. The present invention provides a recombinant, L-amino acid-secreting, coryneform bacterium in which the amtR gene which codes for an AmtR regulator whose amino acid sequence may be at least 85% or at least 90%, preferably at least 95%, particularly preferably at least 98% or at least 99% and very particularly preferably identical to the amino acid sequence of SEQ ID NO:2 and essentially comprises a length of 222 amino acids has been attenuated by one or more of the measures selected from the group a) to v) listed above.

DETAILED DESCRIPTION OF THE PREFERRED EMBODIMENTS

Coryneform bacteria may be employed to produce the bacteria of the invention. Among the coryneform bacteria, the genus *Corynebacterium* may be preferred. Within the genus *Corynebacterium*, strains derived from the following species may be preferred:

*Corynebacterium efficiens*, such as, for example, the type strain DSM44549,

*Corynebacterium glutamicum*, such as, for example, the type strain ATCC13032 or the strain R, and

*Corynebacterium ammoniagenes*, such as, for example, the strain ATCC6871, with very particular preference for the species *Corynebacterium glutamicum*.

Some representatives of the species *Corynebacterium glutamicum* may also be described by other names. These names include, for example:

*Corynebacterium acetoacidophilum* ATCC13870,
*Corynebacterium lilium* DSM20137,
*Corynebacterium melassecola* ATCC17965,
*Brevibacterium flavum* ATCC14067,
*Brevibacterium lactofermentum* ATCC13869, and
*Brevibacterium divaricatum* ATCC14020.

The term "*Micrococcus* glutamicus" for *Corynebacterium glutamicum* has likewise been in use.

Some representatives of the species *Corynebacterium efficiens* have also been referred to as *Corynebacterium thermoaminogenes*, such as, for example, the strain from FERM BP-1539.

The strains of coryneform bacteria (starting strains) employed for the attenuation measures preferably already have the ability to enrich the desired L-amino acid(s) in the cell or secrete them into the nutrient medium surrounding them and accumulate them there. The term "produce" is also used hereinafter to describe this secretion and accumulation.

In particular, the strains of coryneform bacteria employed for the attenuation measures have the ability to enrich or accumulate in the cell or in the nutrient medium at least 0.25 g/l, preferably at least 0.5 g/l, more preferably at least 1.0 g/l, most preferably at least 1.5 g/l, particularly preferably at least 2.0 g/l, more particularly preferably at least 4 g/l or most particularly preferably at least 10 g/l of the desired compound in at most 120 hours, preferably at most 96 hours, more preferably 48 hours, most preferably 36 hours, particularly preferably at most 24 hours or most particularly preferably at most 12 hours. The starting strains may preferably be strains which have been produced by mutagenesis and selection, by recombinant DNA techniques or by a combination of both methods.

It is obvious and requires no further explanation that a bacterium of the invention may also be acquired by firstly attenuating the amtR gene in a wild strain such as, for example, in the type strain ATCC13032 or in the strain ATCC14067, with the aid of the measures of the invention, and subsequently causing the bacterium, by suitable further genetic measures, to produce the desired L-amino acid(s).

The term L-amino acids according to the present invention includes the proteinogenic amino acids, plus L-ornithine and L-homoserine. Proteinogenic L-amino acids include the L-amino acids which occur in natural proteins, that is to say in proteins of microorganisms, plants, animals and humans. The proteinogenic amino acids may include L-aspartic acid, L-asparagine, L-threonine, L-serine, L-glutamic acid, L-glutamine, L-glycine, L-alanine, L-cysteine, L-valine, L-methionine, L-isoleucine, L-leucine, L-tyrosine, L-phenylalanine, L-histidine, L-lysine, L-tryptophan, L-arginine, L-proline, L-selenocysteine and L-pyrrolysine. The preferred L-amino acids may be L-lysine, L-glutamic acid, L-glutamine, L-arginine, L-proline and L-ornithine. L-lysine may be particularly preferred.

The description of amino acids or L-amino acids according to the present invention may include the salts thereof, such as, for example, the lysine monohydrochloride or lysine sulfate in the case of the amino acid L-lysine.

Examples of known representatives of L-lysine-producing or -secreting strains of coryneform bacteria may be:

*Corynebacterium glutamicum* DM58-1/pDM6 (=DSM4697) described in EP 0 358 940,

*Corynebacterium glutamicum* MH20-22B (=DSM16835) described in Menkel et al. (Applied and Environmental Microbiology 55(3), 684-688 (1989)),

*Corynebacterium glutamicum* AHP-3 (=Ferm BP-7382) described in EP 1 108 790,

*Corynebacterium glutamicum* NRRL B-11474 described in U.S. Pat. No. 4,275,157,

*Corynebacterium glutamicum* DSM13994 described in U.S. Pat. No. 6,783,967,

*Corynebacterium glutamicum* DSM16834 described in WO 06/063660,

*Corynebacterium glutamicum* DSM17119 described in WO 06/100211,

*Corynebacterium glutamicum* DSM17223 described in WO 06/125714,

*Corynebacterium glutamicum* DSM16937 described in WO 06/077004, and

*Corynebacterium thermoaminogenes* AJ12521 (=FERM BP-3304) described in U.S. Pat. No. 5,250,423.

Data on the taxonomic classification of strains of the group of coryneform bacteria may be found inter alia in Seiler (Journal of General Microbiology 129, 1433-1477 (1983)), Kinoshita (1985, Glutamic Acid Bacteria, p 115-142. In: Demain and Solomon (ed), Biology of Industrial Microorganisms. The Benjamin/Cummins Publishing Co., London, UK), Kämpfer and Kroppenstedt (Canadian Journal of Microbiology 42, 989-1005 (1996)), Liebl et al (International Journal of Systematic Bacteriology 41, 255-260 (1991)), Fudou et al (International Journal of Systematic and Evolutionary Microbiology 52, 1127-1131 (2002)) and in U.S. Pat. No. 5,250,434.

Strains with the designation "ATCC" may be purchased from the American Type Culture Collection (Manassas, Va., USA). Strains with the designation "DSM" may be purchased from the Deutsche Sammlung von Mikroorganismen and Zellkulturen (DSMZ, Braunschweig, Germany). Strains with the designation "NRRL" may be purchased from the Agricultural Research Service Patent Culture Collection (ARS, Peoria, Ill., US). Strains with the designation "FERM" may be purchased from the National Institute of Advanced Industrial Science and Technology (AIST Tsukuba Central 6, 1-1-1 Higashi, Tsukuba Ibaraki, Japan).

L-Lysine-producing coryneform bacteria typically may have a feedback-resistant or desensitized aspartate kinase. Feedback-resistant aspartate kinases are aspartate kinases (LysC) which, by comparison with the wild form (wild type), show less sensitivity to inhibition by mixtures of lysine and threonine or mixtures of AEC (aminoethylcysteine) and threonine or lysine alone or AEC alone. The genes or alleles coding for these aspartate kinases which are desensitized by comparison with the wild type may also be referred to as $lysC^{FBR}$ alleles. Numerous $lysC^{FBR}$ alleles coding for aspartate kinase variants which have amino acid exchanges by comparison with the wild-type protein are conventionally known. The coding region of the wild-type lysC gene of *Corynebacterium glutamicum* ATCC13032 corresponding to access number AX756575 of the NCBI database is depicted in SEQ ID NO:7 and the polypeptide encoded by this gene is depicted in SEQ ID NO:8. The amino acid sequence of the wild form of aspartate kinase varies slightly in different wild-type strains of *Corynebacterium glutamicum*. Thus, the aspartate kinase of the wild-type strain *Corynebacterium glutamicum* ATCC14067 contains alanine at position 317. The wild-type aspartate kinase of the strain ATCC 13032 contains serine at this position, as depicted in SEQ ID NO:8.

In a preferred embodiment of the present invention, the L-lysine-producing coryneform bacteria have a lysC allele which codes for an aspartate kinase variant which has the amino acid sequence of SEQ ID NO:13, and includes one or more of the amino acid exchanges selected from the group consisting of:

a) LysC A279T (exchange of L-alanine at position 279 of the encoded aspartate kinase protein shown in SEQ ID NO: 13 for L-threonine; see U.S. Pat. No. 5,688,671 and access numbers E06825, E06826, E08178 and I74588 to I74597), b) LysC A279V (exchange of L-alanine at position 279 of the encoded aspartate kinase protein shown in SEQ ID NO: 13 for L-valine; see JP 6-261766 and access number E08179), c) LysC L297Q (exchange of L-leucine at position 297 of the encoded aspartate kinase protein shown in SEQ ID NO: 13 for L-glutamine; see DE 102006026328, d) LysC S301F (exchange of L-serine at position 301 of the encoded aspartate kinase protein shown in SEQ ID NO: 13 for L-phenylalanine; see U.S. Pat. No. 6,844,176 and access number E08180), e) LysC S301Y (exchange of L-serine at position 301 of the encoded aspartate kinase protein shown in SEQ ID NO: 13 for L-tyrosine; see Kalinowski et al. (Molecular and General Genetics 224, 317-324 (1990)) and access number X57226), f) LysC T308I (exchange of L-threonine at position 308 of the encoded aspartate kinase protein shown in SEQ ID NO: 13 for L-isoleucine; see JP 6-261766 and access number E08181),
g) LysC T311I (exchange of L-threonine at position 311 of the encoded aspartate kinase protein shown in SEQ ID NO: 13 for L-isoleucine; see WO 00/63388 and U.S. Pat. No. 6,893,848),
h) LysC R320G (exchange of L-arginine at position 320 of the encoded aspartate kinase protein shown in SEQ ID NO: 13 for glycine; see Jetten et al. (Applied Microbiology and Biotechnology 43, 76-82 (995)) and access number L27125),
i) LysC G345D (exchange of glycine at position 345 of the encoded aspartate kinase protein shown in SEQ ID NO: 13 for L-aspartic acid; see Jetten et al. (Applied Microbiology and Biotechnology 43, 76-82 (995)) and access number L16848),
j) LysC T380I (exchange of L-threonine at position 380 of the encoded aspartate kinase protein shown in SEQ ID NO: 13 for L-isoleucine; see WO 01/49854 and access number AX192358), and
k) LysC S381F (exchange of L-serine at position 381 of the encoded aspartate kinase protein shown in SEQ ID NO: 13 for L-phenylalanine; see EP 0435132), with L-alanine being present where appropriate at position 317 instead of L-serine.

Preferred embodiments of the present invention include the lysC$^{FBR}$ allele lysC T311I (exchange of threonine at position 311 of the encoded aspartate kinase protein shown in SEQ ID NO: 13 for isoleucine) and a lysC$^{FBR}$ allele comprising at least one exchange selected from the group of A279T (exchange of alanine at position 279 of the encoded aspartate kinase protein shown in SEQ ID NO: 13 for threonine), S381F (exchange of serine at position 381 of the encoded aspartate kinase protein shown in SEQ ID NO: 13 for phenylalanine), with the serine at position 317 being exchanged where appropriate for alanine (S317A).

An especially preferred embodiment of the present invention includes the lysC$^{FBR}$ allele lysC T311I (exchange of threonine at position 311 of the encoded aspartate kinase protein shown in SEQ ID NO: 13 for isoleucine), with the serine at position 317 being exchanged where appropriate for alanine (S317A).

The strain DSM 16833 (WO 06/063660) has a lysC$^{FBR}$ allele which codes for an aspartate kinase protein which comprises the amino acid exchange T311I.

The strain NRRL B-11474 (U.S. Pat. No. 4,275,157) has a lysC$^{FBR}$ allele which codes for an aspartate kinase protein which comprises the amino acid exchange S381F. It may also be advantageous for lysine production to overexpress the lysC$^{FBR}$ alleles.

In a further embodiment, the L-lysine-producing bacteria of the genus *Corynebacterium* according to the present invention which preferably additionally comprise a polynucleotide which codes for a lysine-insensitive aspartate kinase variant may have one or more of the measures selected from the group consisting of:
a) overexpressed polynucleotide (dapA gene) which codes for a dihydrodipicolinate synthase (DapA, EC No. 4.2.1.52),
b) overexpressed polynucleotide (asd gene) which codes for an aspartate-semialdehyde dehydrogenase (Asd, EC No. 1.2.1.11),
c) overexpressed polynucleotide (ddh gene) which codes for a meso-diaminopimelate dehydrogenase (Ddh, EC No. 1.4.1.16),
d) overexpressed polynucleotide (lysA gene) which codes for a diaminopimelate decarboxylase (LysA, EC No. 4.1.1.20),
e) overexpressed polynucleotide (aat gene) which codes for an aspartate aminotransferase (Aat, EC No. 2.6.1.1),
f) overexpressed polynucleotide (lysE gene) which codes for a polypeptide having L-lysine export activity (LysE, lysine efflux permease),
g) overexpressed polynucleotide which codes for a pyruvate carboxylase (Pyc, EC No. 6.4.1.1), and
h) overexpressed polynucleotide (dapB gene) which codes for a dihydrodipicolinate synthase (DapB, EC No. 1.3.1.26).

The bacterial genes conventionally known may be used for this purpose. The endogenous genes or polynucleotides of the genus *Corynebacterium* may preferably be used, particularly preferably those of the species *Corynebacterium glutamicum, Corynebacterium efficiens* and *Corynebacterium ammoniagenes* and very particularly preferably those of the species *Corynebacterium glutamicum*.

Endogenous genes or polynucleotides refer to the open reading frames (ORF), genes or alleles, or polynucleotides thereof, which are present in the population of a species.

The dapA gene of *Corynebacterium glutamicum* strain ATCC13032 is described for example in EP 0 197 335. For overexpression of the dapA gene of *Corynebacterium glutamicum* it is additionally possible to employ inter alia the mutations MC20 and MA16 of the dapA promoter as described in U.S. Pat. No. 6,861,246.

The asd gene of *Corynebacterium glutamicum* strain ATCC 21529 is described for example in U.S. Pat. No. 6,927,046.

The lysA gene of *Corynebacterium glutamicum* ATCC13869 (*Brevibacterium lactofermentum*) is described for example in U.S. Pat. No. 6,090,597.

The ddh gene is described for example in Ishino et al. (Agricultural and Biological Chemistry 52(11), 2903-2909 (1988)).

The aat gene of *Corynebacterium glutamicum* ATCC13032 is described for example in Kalinowski et al (Journal of Biotechnology 104 (1-3), 5-25 (2003); see also access number NC_006958). It is referred to therein as the aspB gene. A gene coding for an aspartate aminotransferase is referred to as aspC in U.S. Pat. No. 6,004,773. Marienhagen et al (Journal of Bacteriology 187 (22), 7693-7646 (2005)) refer to the aat gene as aspT gene.

The lysE gene of *Corynebacterium glutamicum* R127 is described for example in U.S. Pat. No. 6,858,406. It may be possible in the same way to employ the lysE gene of the strain ATCC13032 used in U.S. Pat. No. 6,861,246.

The pyc gene of *Corynebacterium glutamicum* of the ATCC 13032 strain is described for example in WO 99/18228 and WO 00/39305. It may also be possible to use alleles of the pyc gene described for example in U.S. Pat. No. 6,965,021. The pyruvate carboxylases described in this patent have one or more of the amino acid exchanges selected from the group: Pyc E153D (exchange of L-glutamic acid at position 153 for L-aspartic acid), Pyc A182S (exchange of L-alanine at position 182 for L-serine), Pyc A206S (exchange of L-alanine at position 206 for L-serine), Pyc H227R (exchange of L-histidine at position 227 for L-arginine), Pyc A455G (exchange of L-alanine at position 455 for glycine), and Pyc D1120E (exchange of L-aspartic acid at position 1120 for L-glutamic acid). It may likewise be possible to use the pyc allele described in EP 1 108 790, which codes for a pyruvate carboxylase which comprises the amino acid exchange Pyc P458S (exchange of L-proline at position 458 for L-serine).

Overexpression conventionally refers to an increase in the intracellular concentration or activity of a ribonucleic acid, of a protein (polypeptide) or of an enzyme by comparison with the starting strain (parent strain) or wild-type strain. A starting strain (parent strain) refers to the strain on which the measure leading to overexpression has been carried out.

The increase in concentration or activity may be achieved for example by increasing the copy number of the appropriate polynucleotides chromosomally or extra-chromosomally by at least one copy.

A conventional method for increasing the copy number consists of incorporating the appropriate polynucleotide into a vector, preferably a plasmid, which is replicated by a coryneform bacterium. It may also be possible to employ transposons, insertion elements (IS elements) or phages as vectors. A large number of suitable vectors are conventionally known.

Another widely used method for achieving overexpression may be the method of chromosomal gene amplification. In this method, at least one additional copy of the polynucleotide of interest is inserted into the chromosome of a coryneform bacterium. Amplification methods of this type are described for example in WO 03/014330 or WO 03/040373.

A further method for achieving overexpression consists of linking the appropriate gene or allele in a functional manner (operably linked) to a promoter or to an expression cassette. Suitable promoters for *Corynebacterium glutamicum* are described for example in FIG. 1 of the review article by Patek et al. (Journal of Biotechnology 104(1-3), 311-323 (2003)). It may be possible in the same way to employ the variants of the dapA promoter which are described by Vasicova et al (Journal of Bacteriology 181, 6188-6191 (1999)), for example the promoter A25. A further possibility may be to use the gap promoter of *Corynebacterium glutamicum* (EP 06007373). Finally, the T3, T7, SP6, M13, lac, tac and trc promoters are described by Amann et al. (Gene 69(2), 301-315 (1988)) and Amann and Brosius (Gene 40(2-3), 183-190 (1985)). A promoter of this type may be inserted for example upstream of the relevant gene, typically at a distance of approximately 1-500 nucleobases from the start codon.

In alternative embodiments of the present invention, the overexpression measures increase the activity or concentration of the appropriate polypeptide by at least 10%, 25%, 50%, 75%, 100%, 150%, 200%, 300%, 400% or 500%, up to a maximum of 1000% or 2000%, based on the activity or concentration of the polypeptide in the strain before the measure leading to the overexpression.

It may be likewise possible, in addition to the measures relating to the amtR gene, to attenuate or switch off individual biosynthesis genes.

In alternative embodiments of the present invention, improving the production of L-lysine, L-valine or L-isoleucine, preferably L-lysine, may be achieved by attenuation or switching off one or more of the genes selected from the group of consisting of:
a) a pgi gene coding for glucose-6-phosphate isomerase (Pgi, EC No. 5.3.1.9), such as, for example, the pgi gene described in U.S. Pat. No. 6,586,214 and U.S. Pat. No. 6,465,238 of *Corynebacterium glutamicum*;
b) an mdh gene coding for malate dehydrogenase (Mdh, EC No. 1.1.1.37), as described for example in WO 02/02778;
c) an mqo gene coding for malate-quinone oxidoreductase (Mqo, EC No. 1.1.99.16), as described for example in U.S. Pat. No. 7,094,106 and PCT/EP2005/057216; and
d) an aceE gene (AceE, EC No. 1.2.4.1) coding for the E1p subunit of the pyruvate dehydrogenase complex, as described for example in EP-A-1767616.

These measures may in the case of L-lysine production also be carried out in addition to the use of lysC$^{FBR}$ alleles and/or overexpression of one or more genes selected from the group of dapA, dapB, asd, ddh, lysA, aat, lysE and pyc.

The term "attenuation" according to the present invention, describes the reduction or switching off of the intracellular activity of one or more enzymes (proteins) in a microorganism which are encoded by the appropriate DNA, by for example using a weak promoter or using a gene or allele which codes for a corresponding enzyme with a low activity, or inactivates the corresponding gene or enzyme (protein) and, optionally, combining these measures.

In the case of the AceE polypeptide (see SEQ ID NO: 2 of EP-A-1767616), the attenuation may also be achieved by one or more of the amino acid exchanges selected from the group consisting of a) exchange of Ala at position 225 for Val, Leu or Ile, preferably Val, b) exchange of Gly at position 255 for Ser or Thr, preferably Ser, c) exchange of Asn at position 282 for Gln, and d) exchange of Cys at position 283 for another amino acid, preferably Ser, with preference for the following amino acid exchanges selected from the group consisting of e) exchange at position 282, f) simultaneous exchange at positions 225 and 283, and g) simultaneous exchange at positions 255 and 283.

The concentration of a protein may be determined by 1- and 2-dimensional protein gel fractionation and subsequent optical identification of the protein concentration in the gel with appropriate analysis software. A common method for preparing the protein gels for coryneform bacteria and for identifying the proteins is the procedure described by Hermann et al. (Electrophoresis, 22:1712-23 (2001)). The protein concentration may likewise be determined via Western blot hybridization with an antibody specific for the protein to be detected (Sambrook et al., Molecular cloning: a laboratory manual. 2$^{nd}$ Ed. Cold Spring Harbor Laboratory Press, Cold Spring Harbor, N.Y., 1989) and subsequent optical analysis with appropriate software for concentration determination (Lohaus and Meyer (1998) Biospektrum 5:32-39; Lottspeich, Angewandte Chemie 38: 2476-2492 (1999)). The activity may be determined with the aid of a suitable enzyme assay.

The AmtR regulator, which is also referred to hereinafter as AmtR polypeptide or AmtR transcription regulator, is a polypeptide having the activity of a transcription regulator which represses expression of the genes of nitrogen metabolism when there is a nitrogen excess in the cell. Derepression takes place when there is a nitrogen deficiency.

When a wild-type strain of a coryneform bacterium, preferably *Corynebacterium glutamicum* such as, for example, strain ATCC 13032, is cultured in a minimal medium which contains ammonium ions as nitrogen source, there may be a nitrogen deficiency when the ammonium ion concentration is less than or equal to 5 mM, preferably less than or equal to 1 mM, particularly preferably less than or equal to 0.5 mM.

The degree of adenylation of the signal transduction protein GlnK in the cytoplasm of the coryneform bacterium likewise gives information on whether there is a nitrogen deficiency or nitrogen excess for the cell. Nitrogen deficiency is present when greater than or equal to 80%, preferably greater than or equal to 90%, particularly preferably greater than or equal to 95% of the signal transduction protein is present in adenylated form in the cell.

The genes of nitrogen metabolism which are repressed by the AmtR regulator when there is a nitrogen excess include, inter alia, amtA, amtB, codA, crnT, gdh, glnA, gluA, gltB, ureA and urtA (Table 1 on p. 584 in Beckers et al. (Molecular Microbiology 58(2), 580-595 (2005)).

The amino acid sequence of the AmtR regulator of coryneform bacteria is at least 85% or at least 90%, preferably at least 95%, particularly preferably at least 98% or at least 99% identical to the amino acid sequence of SEQ ID NO:2 and includes or has essentially a length of 222 amino acids, with preference for a length of 222 amino acids. An example of an AmtR regulator which is at least 98% identical to the amino acid sequence of SEQ ID NO:2 is that of strain ATCC14067. It is listed in SEQ ID NO:21. It is very particularly preferred for the AmtR regulator to include or have the amino acid sequence of SEQ ID NO:2. Where appropriate, the amino acid sequence of SEQ ID NO:2 or 21 comprises not more than 3, preferably not more than 2, particularly preferably not more than one, conservative amino acid exchange(s). The conservative amino acid exchanges essentially do not alter the activity of the AmtR repressor.

The term "essentially a length of 222 amino acids" includes consideration that the length of the encoded polypeptide varies slightly in different species or strains of L-amino acid-secreting coryneform bacteria through insertion or deletion of one (1) or more, not more than 10, 9, 8, 7, 6, 5, 4, 3 or 2, amino acids within the polypeptide or at the N- or C-terminal end of the polypeptide. One example thereof is the AmtR regulator of *Corynebacterium efficiens*. The length of the polypeptide (see SEQ ID NO:11) is in this case 223 amino acids. The different length of the AmtR regulator is caused by insertion of the amino acid L-glutamic acid between position 151 and 153 of SEQ ID NO:2.

The relation between the amino acids of the amino acid sequence of the AmtR regulator of *Corynebacterium efficiens* (AmtR Ceff) and the amino acids of the amino acid sequence of the AmtR regulator of *Corynebacterium glutamicum* (AmtR Cglu) is shown below.

```
AmtR Ceff 1
magavgrprrsaprragknpreeildasaelftrqgfattsthqiadavg

AmtR Cglu 1
magavgrprrsaprragknpreeildasaelftrqgfattsthqiadavg

AmtR Ceff 51
irqaslyyhfpskteifltllkstvepsmvlagdlanleaspelrlwalv

AmtR Cglu 51
irqaslyyhfpskteiflfllkstvepstvlaedlstldagpemrlwaiv

AmtR Ceff 101
aaevrlllstkwnvgrlyqlpivaseefeeyhtqratltdtfrslateiv

AmtR Cglu 101
asevrlllstkwnvgrlyqlpivgseefaeyhsqrealtnvfrdlateiv

AmtR Ceff 151
geddpraelpfhitmsaiemrrndgkvpsplsedslpdtavmladaalav

AmtR Cglu 151
g-ddpraelpfhitmsviemrrndgkipsplsadslpetaimladaslav (SEQ ID NO: 11)
AmtR Ceff 201
lgadlpgdrvertlellrqadak (SEQ ID NO: 2)
AmtR Cglu 200
lgaplpadrvektlelikqadak
```

It may also be possible to use so-called alignment programs such as, for example, the ClustalW (Thompson et al., Nucleic Acids Research 25(24), 4876-82 (1997)) or MAFFT program (Katoh et al., Nucleic Acid Res., 30:3059-3066 (2002)) for relating the individual amino acids of different AmtR regulators. The individual amino acids of a polypeptide can thus be unambiguously related to one another, despite the amino acid sequences formally differing in length.

In the case of aromatic L-amino acids, mutual exchanges of L-phenylalanine, L-tryptophan and L-tyrosine are referred to as conservative exchanges. In the case of hydrophobic L-amino acids, mutual exchanges of L-leucine, L-isoleucine and L-valine are referred to as conservative exchanges. In the case of polar amino acids, mutual exchanges of L-glutamine and L-asparagine are referred to as conservative exchanges. In the case of basic amino acids, mutual exchanges of L-arginine, L-lysine and L-histidine are referred to as conservative exchanges. In the case of acidic L-amino acids, mutual exchanges of L-aspartic acid and L-glutamic acid are referred to as conservative exchanges. In the case of amino acids containing hydroxyl groups, mutual exchanges of L-serine and L-threonine are referred to as conservative exchanges.

The expression "essentially do not alter the activity of the AmtR repressor" means that, by the not more than 3 conservative amino acid exchanges, the ability of the AmtR repressor to bind to its DNA binding site is altered by not more than 10%, preferably not more than 5%, particularly preferably not more than 1% and very particularly preferably is unaltered. The activity may be measured by retardation gel electrophoresis (gel retardation assay) using double-stranded DNA molecules with the nucleotide sequence of an AmtR binding site of the amtA gene (see SEQ ID NO:14 and 15), of an AmtR binding site of the amtB gene (see SEQ ID NO:16 and 17) or of an AmtR binding site of the gltB gene (see SEQ ID NO:18 and 19), preferably using double-stranded DNA molecules with the nucleotide sequence of an AmtR binding site of the amtA gene and very particularly preferably using a double-stranded DNA molecule with the nucleotide sequence of SEQ ID NO:14. The nucleotide sequences are taken from Table 1 of Beckers et al. (Molecular Microbiology 58(2), 580-595 (2005)).

SEQ ID NO: 1 represents the nucleotide sequence of the coding region of the amtR gene of the type strain of *Corynebacterium glutamicum* (wild-type gene), that is ATCC13032, according to the data in the National Center for Biotechnology Information (NCBI) database. SEQ ID NO:2 and 4 show the amino acid sequence of the encoded polypeptide. SEQ ID NO:2 and 4 comprise L-arginine at position 34, L-threonine at position 87 and L-proline at position 203. It is known that the terminal methionine can be deleted in the protein synthesis by host-intrinsic enzymes, called amino peptidases. SEQ ID NO:3 additionally indicates nucleotide sequences located upstream and downstream.

SEQ ID NO: 10 represents the nucleotide sequence of the coding region of the amtR gene of *Corynebacterium efficiens* strain YS-314 according to the data in the National Center for Biotechnology Information (NCBI) database. SEQ ID NO:11 shows the amino acid sequence of the encoded polypeptide.

SEQ ID NO: 20 represents the nucleotide sequence of the coding region of the amtR gene of *Corynebacterium glutamicum* ATCC14067. The sequence was determined by the applicant. SEQ ID NO:21 shows the amino acid sequence of the encoded polypeptide. The amino acid sequence of SEQ ID NO:21 comprises L-histidine at position 34, L-isoleucine at position 87 and L-serine at position 203.

The nucleotide sequence of the genome of *Corynebacterium glutamicum* has been determined by various research groups.

The sequence of the strain ATCC13032 which was determined by Kalinowski et al. (Journal of Biotechnology 104(1-3), 5-25 (2003)) of Bielefeld University (Germany) is available under access number NC_006985. The name assigned to the amtR gene therein is cg0986 and includes the region of position 923864-924532 of the complementary strand.

The sequence of the strain ATCC13032 determined by Ikeda and Nakagawa (Applied Microbiology 62(2-3), 99-109 (2003)) of Kitasato University (Japan) is available under the access number NC_003450. The name assigned to the amtR gene therein is NCgl0828.

The sequence of strain R determined by Yukawa et al. (Microbiology 153 (Pt 4), 1042-58 (2007)) of the Research Institute of Innovative Technology for the Earth (RITE) (Japan) is available under the access number NC_009342. The name assigned to the amtR gene therein is cgR_0978.

The nucleotide sequence of the genome of *Corynebacterium efficiens* was determined by Nishio et al. (Genome Research 2003 13(7), 1572-1579 (2003)) of Ajinomoto Co. Inc. (Japan). It is available under the access number NC_004369. The name assigned to the amtR gene therein is COG1309K and includes the region of position 1002436-1003107 of the complementary strand.

The AmtR regulator belongs to the TetR family of transcription regulators and has, like the other members of this family, a typical helix-turn-helix motif at the DNA binding site (Ramos et al., Microbiology and Molecular Biology Reviews 69(2): 326-356 (2003); Jacoby et al., Molecular Microbiology 37(4): 964-977 (2000)).

The nucleotide sequences of the DNA to which the AmtR regulator binds are known. Jakoby et al. (Molecular Microbiology 37(4), 964-977 (2000)) investigated, by deletion analyses, retardation gel electrophoresis (gel retardation assay) and the Matchmaker One-Hybrid system (Clontech Laboratories, Inc., Mountain View, USA), the expression of the amt gene which codes for the ammonium transporter Amt in *Corynebacterium glutamicum* (Siewe et al., Journal of Biological Chemistry 271 (10): 5398-5402 (1996)). The ammonium transporter Amt is also referred to as (methyl) ammonium uptake system in Jakoby et al. In Beckers et al. (Molecular Microbiology 58 (2), 580-595 (2005)), the amt gene is referred to as amtA gene. It has the NCBI access number NCgl1521. Jakoby et al. showed that expression of the amt gene is repressed through binding of the AmtR regulator to binding motifs of double-stranded DNA having the nucleotide sequence 5'-ATCTATAGAACGATAG-3' (SEQ ID NO: 22) and 5'-ATCTATAGGCGGATAG-3' (SEQ ID NO: 23).

Beckers et al. (Molecular Microbiology 58(2), 580-595 (2005)) determined the consensus motif of the binding site for the genes regulated by the AmtR regulator. Beckers et al., in contrast to Jakoby et al. (Molecular Microbiology 37 (4), 964-977 (2000)), indicate the nucleotide sequence of the reverse complementary DNA strand of the binding site.

Further details on the AmtR regulator may be found inter alia in Walter et al. (Journal of Molecular Microbiology 12, 131-138 (2007)) and A. Burkovski (Archives of Microbiology 179: 83-88 (2003); Article "Nitrogen Metabolism and its Regulation" in the "Handbook of *Corynebacterium glutamicum*" (Eds.: L. Eggeling and M. Bott, CRC Press, Taylor & Francis, 2005).

The term "attenuation" entails reducing the intracellular concentration or activity of one or more polypeptides (proteins) or enzymes in a microorganism which are encoded by the appropriate DNA compared with the parent strain. The strain referred to as parent strain or starting strain is the one on which the attenuation measures have been carried out. The attenuation can be achieved by reducing the expression of a polypeptide, for example by using a weak promoter, or by using an allele which codes for a polypeptide having a lower activity and, where appropriate, inactivates these measures.

The promoter region of the amtR gene is depicted in SEQ ID NO:5. The nucleotide sequence of SEQ ID NO:5 is present in SEQ ID NO:3. Position 1 of SEQ ID NO:5 corresponds to position 911 of SEQ ID NO:3. Position 90 of SEQ ID NO:5 corresponds to position 1000 of SEQ ID NO:3.

In alternative embodiments of the present invention, expression of the AmtR regulator may be reduced by one or more of the modifications of the promoter region of the amtR gene selected from the group consisting of:

a. replacement of the nucleobase guanine at position 7 of the promoter region of the amtR gene shown in SEQ ID NO:5 by thymine, b. replacement of the nucleobase cytosine at position 11 of the promoter region of the amtR gene shown in SEQ ID NO:5 by guanine, c. replacement of the nucleobase thymine at position 40 of SEQ ID NO:5 by guanine, d. replacement of the nucleobase thymine at position 45 of the promoter region of the amtR gene shown in SEQ ID NO:5 by guanine, e. deletion of one or more of the nucleobases of position 40 to 45, preferably deletion of all nucleobases of position 40 to 45, of the promoter region of the amtR gene shown in SEQ ID NO:5, f. deletion of one or more of the nucleobases between position 72 and 78 of the promoter region of the amtR gene shown in SEQ ID NO:5, and g. replacement of one or more of the nucleobases adenine or guanine between position 72 and 78 of the promoter region of the amtR gene shown in SEQ ID NO:5 by thymine or cytosine.

Expression of the AmtR regulator may be further reduced according to the present invention by exchange of the ATG start codon at position 1 to 3 of the coding region of the amtR gene for a GTG or TTG start codon.

In alternative embodiments of the present invention the reduction in the expression of the amtR gene may diminish the intracellular concentration of the AmtR regulator to greater than 0% to less than or equal to 75%, greater than 0% to less than or equal to 50%, greater than 0% to less than or equal to 25%, greater than 0% to less than or equal to 5%, greater than 0% to less than or equal to 1%, or to greater than or equal to 0.1% to less than or equal to 75%, greater than or equal to 0.1% to less than or equal to 50%, greater than or equal to 0.1% to less than or equal to 25%, greater than or equal to 0.1% to less than or equal to 5%, greater than or equal to 0.1% to less than or equal to 1%, or to greater than or equal to 1% to less than or equal to 75%, greater than or equal to 1% to less than or equal to 50%, greater than or equal to 1% to less than or equal to 25%, greater than or equal to 1% to less than or equal to 5%, or to greater than or equal to 5% to less than or equal to 75%, greater than or equal to 5% to less than or equal to 50%, greater than or equal to 5% to less than or equal to 25% of the concentration in the parent strain or starting strain.

In alternative embodiments of the present invention the activity of the AmtR regulator may be reduced by one or more, preferably not more than 3, particularly preferably not more than 2, of the amino acid exchanges selected from the group consisting of:

a. exchange of the glycine at position 3 of the amino acid sequence, preferably the amino acid sequence shown in SEQ ID NO:2, SEQ ID NO:21 or SEQ ID NO:11, for another proteinogenic L-amino acid, preferably L-glutamic acid or L-aspartic acid, particularly preferably L-glutamic acid, b. exchange of the L-isoleucine at position 24 of the amino acid sequence, preferably the amino acid sequence shown in SEQ ID NO:2, SEQ ID NO:21 or SEQ ID NO:11, for an amino acid selected from the group of L-asparagine, L-glutamine, L-glutamic acid and L-aspartic acid, preferably L-aspartic acid, c. exchange of the L-leucine at position 31 of the amino acid sequence, preferably the amino acid sequence shown in SEQ ID NO:2, SEQ ID NO:21 or SEQ ID NO:11, for an amino acid selected from the group of L-proline, L-asparagine, L-glutamine, L-phenylalanine, L-tyrosine, L-tryptophan, L-glutamic acid and L-aspartic acid, preferably L-proline, d. exchange of the L-phenylalanine at position 32 of the amino acid sequence, preferably the amino acid sequence shown in SEQ ID NO:2, SEQ ID NO:21 or SEQ ID NO:11, for an amino acid selected from the group of glycine, L-glutamic acid, L-aspartic acid, L-proline and L-cysteine, preferably L-proline, e. exchange of the glycine at position 36 of the amino acid sequence, preferably the amino acid sequence shown in SEQ ID NO:2, SEQ ID NO:21 or SEQ ID NO:11, for an amino acid selected from the group of L-glutamic acid, L-aspartic acid, L-isoleucine, L-histidine and L-phenylalanine, preferably L-histidine, L-glutamic acid or L-aspartic acid, very particularly preferably L-aspartic acid f. exchange of the L-threonine at position 42 of the amino acid sequence, preferably the amino acid sequence shown in SEQ ID NO:2, SEQ ID NO:21 or SEQ ID NO:11, for an amino acid selected from the group of L-proline, L-isoleucine, L-methionine, L-glutamine, L-tryptophan, L-glutamic acid and L-aspartic acid, preferably L-glutamic acid, g. exchange of the glycine at position 50 of the amino acid sequence, preferably the amino acid sequence shown in SEQ ID NO:2, SEQ ID NO:21 or SEQ ID NO:11, for an amino acid selected from the group of L-glutamic acid, L-aspartic acid, L-isoleucine, L-histidine, L-tryptophan and L-phenylalanine, preferably L-tryptophan, h. exchange of the L-glutamine at position 53 of the amino acid sequence, preferably the amino acid sequence shown in SEQ ID NO:2, SEQ ID NO:21 or SEQ ID NO:11, for an amino acid selected from the group of L-cysteine, L-methionine, L-tyrosine, L-tryptophan and L-phenylalanine, preferably L-phenylalanine, i. exchange of the L-alanine at position 54 of the amino acid sequence, preferably the amino acid sequence shown in SEQ ID NO:2, SEQ ID NO:21 or SEQ ID NO:11, for an amino acid selected from the group of L-phenylalanine, L-isoleucine, L-tryptophan, L-tyrosine, L-histidine, L-glutamic acid and L-aspartic acid, preferably L-histidine, j. exchange of the L-serine at position 55 of the amino acid sequence, preferably the amino acid sequence shown in SEQ ID NO:2, SEQ ID NO:21 or SEQ ID NO:11, for an amino acid selected from the group of L-proline, L-phenylalanine, L-tryptophan, L-lysine, L-arginine, L-glutamic acid and L-aspartic acid, preferably L-phenylalanine, k. exchange of the L-tyrosine at position 57 of the amino acid sequence, preferably the amino acid sequence shown in SEQ ID NO:2, SEQ ID NO:21 or SEQ ID NO:11, for an amino acid selected from the group of L-proline, glycine, L-methionine, L-glutamic acid and L-aspartic acid, preferably L-aspartic acid, l. exchange of the L-tyrosine at position 58 of the amino acid sequence, preferably the amino acid sequence shown in SEQ ID NO:2, SEQ ID NO:21 or SEQ ID NO:11, for an amino acid selected from the group of L-proline, L-methionine and L-cysteine, preferably L-proline, m. exchange of the L-histidine at position 59 of the amino acid sequence, preferably the amino acid sequence shown in SEQ ID NO:2 or SEQ ID NO:11, for an amino acid selected from the group of L-lysine, L-aspartic acid, L-isoleucine, L-proline and glycine, preferably L-proline, and n. exchange of the L-lysine at position 63 of the amino acid sequence, preferably the amino acid sequence shown in SEQ ID NO:2, SEQ ID NO:21 or SEQ ID NO:11, for an amino acid selected from the group of L-alanine, L-glutamic acid, L-aspartic acid, L-asparagine, L-tyrosine and L-tryptophan, preferably L-asparagine.

Preferred embodiments of the present invention may include exchange of the glycine at position 3 of the amino acid sequence and exchange of the glycine at position 36 of the amino acid sequence.

In alternative embodiments of the present invention the amino acid exchanges according to the invention may reduce the activity of the AmtR regulator to ranges including greater than 0% to less than or equal to 75%, greater than 0% to less than or equal to 50%, greater than 0% to less than or equal to 25%, greater than 0% to less than or equal to 5%, greater than 0% to less than or equal to 1%, or to greater than or equal to 0.1% to less than or equal to 75%, greater than or equal to 0.1% to less than or equal to 50%, greater than or equal to 0.1% to less than or equal to 25%, greater than or equal to 0.1% to less than or equal to 5%, greater than or equal to 0.1% to less than or equal to 1%, or to greater than or equal to 1% to less than or equal to 75%, greater than or equal to 1% to less than or equal to 50%, greater than or equal to 1% to less than or equal to 25%, greater than or equal to 1% to less than or equal to 5% or to greater than or equal to 5% to less than or equal to 75%, greater than or equal to 5% to less than or equal to 50%, greater than or equal to 5% to less than or equal to 25% of the activity of the AmtR regulator of the wild type, preferably having the amino acid sequence of SEQ ID NO:2 or SEQ ID NO:11.

In a further embodiment of the present invention it may be additionally possible to decrease or adjust the expression of the variants according to the invention of the AmtR regulator by using known weak promoters. These include inter alia the promoters seqP-RBS_01 to seqP-RBS_07 which are published in the periodical Research Disclosure under the number 512057 (December 2006 edition), and the variants of the dapA promoter described by M. Patek, preferably the variants C7, C13, O1, C2, J2, B31, C5 and B6 (M. Patek in the "Handbook of *Corynebacterium glutamicum*" (Lothar Eggeling and Michael Bott (editors), CRC Press, Taylor and Francis Group, Boca Raton, Fla., USA, 2005)).

The attenuation of the amtR gene may be determined with various methods. The concentration can be detected with the aid of one- and two-dimensional protein gel fractionation and subsequent determination of the protein concentration in the gel. A common method for preparing the protein gels for coryneform bacteria and for identifying the proteins is the procedure described by Hermann et al. (Electrophoresis, 22:1712-23 (2001)). The protein concentration can furthermore be analyzed via Western blot hybridization with an antibody specific for the protein to be detected (Sambrook et al., Molecular cloning: a laboratory manual. $2^{nd}$ Ed. Cold Spring Harbor Laboratory Press, Cold Spring Harbor, N.Y., 1989) and subsequent optical analysis with appropriate software for concentration determination (Lohaus and Meyer (1998) Biospektrum 5:32-39; Lottspeich, (1999) Angewandte Chemie 111: 2630-2647). The activity of the AmtR regulator as DNA-binding protein can be measured by retardation gel electrophoresis (Wilson et al. (2001) Journal of Bacteriology 183:2151-2155). This assay is also referred to as the DNA band shift assay. The effect of DNA-binding proteins on the expression of the genes controlled by them can also be detected by various well-described methods of the reporter gene assay (Sambrook et al., Molecular cloning: a laboratory manual. $2^{nd}$ Ed. Cold Spring Harbor Laboratory Press, Cold Spring Harbor, N.Y., 1989).

In another embodiment, the invention relates to an isolated polynucleotide comprising the promoter region or essentially consisting of the promoter region of the amtR gene shown in SEQ ID NO:5 having one or more of the modifications according to the invention.

In alternative embodiments of the present invention the promoter region of the amtR gene includes at most 5000, at most 4000, at most 3000, at most 2000, at most 1000, at most 750, at most 500, at most 250, or at most 100 nucleobases or base pairs on nucleotide sequences which naturally flank the promoter region according to the invention upstream and downstream.

The term "natural" also includes nucleotide sequences which comprise the mutations according to the invention.

In another alternative embodiment the present invention includes an isolated polynucleotide including the coding region or essentially consisting of the coding region of the amtR gene which codes for a polypeptide having the amino acid sequence shown in SEQ ID NO:2 or 21, using a GTG or TTG start codon instead of the ATG start codon.

According to this embodiment, the invention is directed to an isolated polynucleotide coding for an AmtR regulator whose amino acid sequence may be at least 85% or at least 90%, preferably at least 95%, particularly preferably at least 98% or at least 99% and very particularly preferably identical to the amino acid sequence of SEQ ID NO:2 and includes or has essentially a length of 222 amino acids, preferably a length of 222 amino acids, and includes one (1) or more, preferably not more than 3, particularly preferably not more than 2, of the amino acid exchanges at positions 3, 24, 31, 32, 36, 42, 50, 53, 54, 55, 57, 58, 59 and 63 according to the invention.

According to this embodiment, preference may be given to an isolated polynucleotide which codes for an AmtR regulator which includes or has the amino acid sequence of SEQ ID NO:2 and which includes one (1) or more, preferably not more than 3, particularly preferably not more than 2, of the amino acid exchanges at positions 3, 24, 31, 32, 36, 42, 50, 53, 54, 55, 57, 58, 59 and 63 according to the present invention. In alternative embodiments the amino acid sequence may comprise not more than 3, preferably not more than 2, particularly preferably not more than (one) conservative amino acid exchange(s).

A further embodiment of the present invention comprises an isolated polynucleotide which codes for an AmtR regulator which includes or has the amino acid sequence of SEQ ID NO:11 and which includes one (1) or more, preferably not more than 3, particularly preferably not more than 2, of the amino acid exchanges at positions 3, 24, 31, 32, 36, 42, 50, 53, 54, 55, 57, 58, 59 and 63 according to the invention. The amino acid sequence may additionally comprise not more than 3, preferably not more than 2, particularly preferably not more than (one) conservative amino acid exchange(s).

In another embodiment of the present invention comprises an isolated polynucleotide which codes for an AmtR regulator which includes or has the amino acid sequence of SEQ ID NO:21 and which includes one (1) or more, preferably not more than 3, particularly preferably not more than 2, of the amino acid exchanges at positions 3, 24, 31, 32, 36, 42, 50, 53, 54, 55, 57, 58, 59 and 63 according to the invention. The amino acid sequence preferably comprises not more than (one) conservative amino acid exchange(s).

An example of a conservative amino acid exchange is exchange of valine at position 141 of the amino acid sequence for isoleucine.

An additional embodiment of the present invention comprises an isolated polynucleotide which codes for an AmtR regulator having the amino acid sequence of SEQ ID NO:2, where the glycine at position 3 is exchanged for another proteinogenic amino acid, preferably L-glutamic acid or L-aspartic acid, particularly preferably L-glutamic acid. The amino acid sequence of the variant of the AmtR polypeptide which comprises L-glutamic acid at position 3 is depicted in SEQ ID NO:6 and 8.

Another embodiment of the present invention comprises an isolated polynucleotide which codes for an AmtR regulator having the amino acid sequence of SEQ ID NO:2, where the glycine at position 36 is exchanged for another proteinogenic amino acid, preferably L-histidine, L-glutamic acid or L-aspartic acid, very particularly preferably L-aspartic acid.

An additional embodiment of the present invention comprises an isolated polynucleotide which includes or has the nucleotide sequence shown in SEQ ID NO:5 or 7.

Further additional alternative embodiments of the present invention comprise an isolated polynucleotide coding for at least a part of the amino acid sequence of the AmtR polypeptide which includes at least 5, at least 10, at least 20, at least 40, at least 80 or at least 100 amino acids and which comprises at least one amino acid exchange according to the invention in the AmtR polypeptide, where the mutation leading to the amino acid exchange according to the invention in the polynucleotide is flanked by nucleotide sequences having a length of at most 5000, at most 4000, at most 3000, at most 2000, at most 1000, at most 750, at most 500, at most 250, or at most 100 nucleobases or base pairs upstream and downstream, which naturally occurs in coryneform bacteria.

Thus, for example, a polynucleotide having the nucleotide sequence from position 500 to 1510 of SEQ ID NO:8 comprises a part of the coding region of the amtR gene which codes for an amino acid sequence having a length of 170 amino acids, this having the amino acid exchange according to the invention at position 3 of the AmtR polypeptide, and a nucleotide sequence having a length of at least 500 nucleobases upstream and downstream of the mutation leading to the amino acid exchange, as occurs naturally in *Corynebacterium glutamicum*.

Further embodiments of the present invention comprise vectors which comprise the polynucleotides according to the invention.

An embodiment of the present invention comprises cells of microorganisms, especially of bacteria, preferably of the genus *Corynebacterium* and *Escherichia*, particularly preferably of the species *Corynebacterium glutamicum* and *Escherichia coli*, which comprise polynucleotides or vectors according to the present invention or have been produced using polynucleotides or vectors according to the present invention.

The polynucleotides according to the invention may be produced by using classical in vivo mutagenesis methods with cell populations of bacteria of the genus *Corynebacterium* using mutagenic substances such as, for example, N-methyl-N'-nitro-N-nitrosoguanidine (MNNG) or ultraviolet light. Subsequently DNA may be prepared or isolated from the mutants, and the corresponding polynucleotide may be synthesized with the aid of the polymerase chain reaction (PCR) using primer pairs which allow amplification of the amtR gene or amtR allele, and may be isolated. It is possible to select for this purpose any primer pairs from the nucleotide sequence located upstream and downstream of the coding region and of the nucleotide sequence complementary thereto.

Instructions and information on PCR may be found by the skilled person for example in the handbook "PCR-Strategies" (Innis, Felfand and Sninsky, Academic Press, Inc., 1995), in the handbook by Diefenbach and Dveksler "PCR Primer—a laboratory manual" (Cold Spring Harbor Laboratory Press, 1995), in the handbook by Gait "Oligonukleotide synthesis: A Practical Approach" (IRL Press, Oxford, UK, 1984) and in Newton and Graham "PCR" (Spektrum Akademischer Verlag, Heidelberg, Germany, 1994). Further instructions on PCR may be found for example in WO 06/100177 on pages 15 to 17.

In a further operation, the nucleotide sequence of the polynucleotide is then determined. This may be determined for example by the chain termination method of Sanger et al. (Proceedings of the National Academies of Sciences, U.S.A., 74, 5463-5467 (1977)) with the modifications indicated by Zimmermann et al. (Nucleic Acids Research 18, 1067 (1990)).

The polypeptide encoded by this nucleotide sequence may then be analyzed for the amino acid sequence. For this purpose, the nucleotide sequence is entered in a program for translating DNA sequence into an amino acid sequence. Suitable programs are for example the "Patentin" program which is obtainable from patent offices, for example the US Patent Office (USPTO), or the "Translate Tool" which is available on the ExPASy Proteomics Server in the World Wide Web (Gasteiger et al., Nucleic Acids Research 31, 3784-3788 (2003)).

It may also be possible to produce the polynucleotide or amtR allele according to the present invention by in vitro genetic methods.

Suitable methods for in vitro mutagenesis may include inter alia treatment with hydroxylamine according to Miller (Miller, J. H.: A Short Course in Bacterial Genetics. A Laboratory Manual and Handbook for *Escherichia coli* and Related Bacteria, Cold Spring Harbor Laboratory Press, Cold Spring Harbor, 1992) or employment of a polymerase chain reaction using a DNA polymerase which shows a high error rate. Such a DNA polymerase is for example the mutazyme DNA polymerase (GeneMorph PCR Mutagenesis Kit, No. 600550) supplied by Stratagene (LaJolla, Calif., USA). A further possibility is to employ mutagenic oligonucleotides as described by T. A. Brown (Gentechnologie für Einsteiger, Spektrum Akademischer Verlag, Heidelberg, 1993) and R. M. Horton (PCR-Mediated Recombination and Mutagenesis, Molecular Biotechnology 3, 93-99 (1995)). The method using the "Quik Change Site-directed Mutagenesis Kit" supplied by Stratagene (La Jolla, Calif., USA), described by Papworth et al. (Strategies 9(3), 3-4 (1996)), may likewise be employed.

The polynucleotides produced by the methods described may be used to produce recombinant strains of the genus *Corynebacterium*, preferably *Corynebacterium glutamicum*, which comprise the variants according to the invention of the AmtR regulator and/or comprise the modifications according to the invention in the promoter region of the amtR gene and which, compared with the starting or parent strain, release L-amino acids into the medium surrounding them and/or accumulate them in the interior of the cell to an increased extent.

A conventional method for incorporating mutations into genes of bacteria of the genus *Corynebacterium*, especially of the species *Corynebacterium glutamicum*, is that of allele exchange which is also known under the name gene replacement. In this method, a DNA fragment which comprises the mutation of interest is transferred into the desired strain, and the mutation is incorporated by at least two recombination events or crossover events into the chromosome of the desired strain, or the sequence of a gene present in the relevant strain is exchanged for the mutated sequence.

The DNA fragment comprising the mutation of interest is in this method typically present in a vector, in particular a plasmid, which preferably undergoes only limited, i.e. under selected culture conditions, or no replication by the strain to be provided with the mutation. In general, a bacterium of the genus *Escherichia*, preferably of the species *Escherichia coli*, may be used as auxiliary or intermediate host in which the vector may be replicated.

Examples of such plasmid vectors are the pK*mob and pK*mobsacB vectors such as, for example, pK18mobsacB, which are described by Schafer et al. (Gene 145, 69-73 (1994)), and the vectors described in WO 02/070685 and WO 03/014362. These are replicative in *Escherichia coli* but not in *Corynebacterium*. Particularly suitable vectors are those comprising a gene with a conditionally negatively dominant effect such as, for example, the sacB gene (levansucrase gene) of, for example, *Bacillus* or the galK gene (galactose kinase gene) of, for example, *Escherichia coli*. A gene with a conditionally negatively dominant effect is a gene which under certain conditions may be disadvantageous, for example toxic, for the host but, under other conditions, has no negative effects on the host harboring the gene. A conditionally negative dominant effect gene makes it possible to select for recombinations events in which the vector is eliminated from the chromosome.

In addition, Nakamura et al. (U.S. Pat. No. 6,303,383) have described a temperature-sensitive plasmid for *Corynebacterium* which is able to replicate only at temperatures below 31° C. It may likewise be employed for the purposes of the present invention. The vector may be subsequently transferred into the *Corynebacterium* by conjugation, for example by the method of Schäfer (Journal of Bacteriology 172, 1663-1666 (1990)) or transformation for example by the method of Dunican and Shivnan (Bio/Technology 7, 1067-1070 (1989)). The transfer of the DNA may also be achieved where appropriate by ballistic methods (e.g. particle bombardment).

Homologous recombination occurring in a first crossover event which brings about integration, and of a suitable second crossover event which brings about an excision in the target gene or in the target sequence achieves incorporation of the mutation and results in a recombinant bacterium. The gene in which the desired exchange is to take place is referred to as target gene.

Methods which may be employed for identifying and characterizing the resulting strains are inter alia those of Southern blotting hybridization, of the polymerase chain reaction, of sequence determination, the method of fluorescence resonance energy transfer (FRET) (Lay et al. Clinical Chemistry 43, 2262-2267 (1997)) or methods of enzymology.

Schwarzer and Pühler (Bio/Technology 9, 84-87 (1991)) used this method to incorporate a lysA allele which harbored a deletion, and a lysA allele which harbored an insertion, into the chromosome of *C. glutamicum* instead of the wild-type gene. Nakagawa et al. (EP 1108790) and Ohnishi et al. (Applied Microbiology and Biotechnology 58(2), 217-223 (2002)) employed this method to incorporate various mutations starting from the isolated alleles or polynucleotides into the chromosome of *C. glutamicum*.

Thus, for example, to incorporate the mutation which leads to exchange of the amino acid glycine for L-glutamic acid at position 3 of SEQ ID NO:2, preferably as depicted in SEQ ID NO:6 and 8, it may be possible to use a polynucleotide or DNA fragment which includes at least the nucleotide sequence from position 958 to 1058 of SEQ ID NO:8. This DNA fragment comprises the mutation according to the invention and, upstream and downstream thereof, a nucleotide sequence having a length of in each case at least 50 nucleobases.

Preferred DNA fragments according to the present invention have, upstream and downstream of the mutation, a nucleotide sequence having a length of in each case at least about 100, particularly preferably in each case at least about 250 nucleobases and very particularly preferably in each case at least about 500 nucleobases. In alternative embodiments of the present invention the maximum length of the nucleotide sequence located upstream and downstream of the mutation may generally be about 500, about 750, about 1000, about 1500, about 2000, about 3000, about 4000 or 5000 nucleobases. Accordingly, in alternative embodiments of the present invention the total length of the polynucleotide employed for the allele exchange is not more than about 1000, not more than about 1500, not more than about 2000, not more than about 3000, not more than about 4000, not more than about 6000, not more than about 8000 or 10 000 nucleobases.

In the alternative embodiments the output of the bacteria of the genus *Corynebacterium* and of the fermentation process using the same according to the present invention in terms of one or more of the parameters selected from the group of the L-amino acid concentration (L-amino acid produced per volume), the L-amino acid yield (L-amino acid produced per carbon source consumed), the L-amino acid production (L-amino acid produced per volume and time) and the specific L-amino acid production (L-amino acid produced per cell dry matter or dry biomass and time or L-amino acid produced per cellular protein and time) or else other process parameters and combinations thereof may be increased by at least 0.5%, at least 1%, at least 1.5% or at least 2% based on the starting strain or parent strain or the fermentation process using the same.

The bacteria produced according to the invention of the genus *Corynebacterium* may be cultured continuously—as described for example in WO 05/021772—or discontinuously in a batch process (batch cultivation or batch process) or in a fed batch or repeated fed batch process for the purpose of producing the desired L-amino acids. A summary of a general nature about known cultivation methods is available in the textbook by Chmiel (Bioprozesstechnik 1. Einführung in die Bioverfahrenstechnik (Gustav Fischer Verlag, Stuttgart, 1991)) or in the textbook by Storhas (Bioreaktoren and periphere Einrichtungen (Vieweg Verlag, Braunschweig/Wiesbaden, 1994)). The culture medium or fermentation medium to be used must satisfy in a suitable manner the demands of the respective strains. Descriptions of culture media for various microorganisms are present in the handbook "Manual of Methods for General Bacteriology" of the American Society for Bacteriology (Washington D.C., USA, 1981). According to the present invention, the terms culture medium and fermentation medium or medium are mutually exchangeable.

According to the various embodiments of the present invention, sugars and carbohydrates such as, for example, glucose, sucrose, lactose, fructose, maltose, molasses, sucrose-containing solutions from sugar beet or sugar cane production, starch, starch hydrolyzate and cellulose, oils and fats such as, for example, soybean oil, sunflower oil, peanut oil and coconut fat, fatty acids such as, for example, palmitic acid, stearic acid and linoleic acid, alcohols such as, for example, glycerol, methanol and ethanol and organic acids such as, for example, acetic acid or lactic acid may be used as the carbon source.

According to the various embodiments of the present invention, organic nitrogen-containing compounds such as peptone, yeast extract, meat extract, malt extract, corn steep liquor, soybean flour and urea and inorganic compounds such as ammonium sulfate, ammonium chloride, ammonium phosphate, ammonium carbonate and ammonium nitrate, may be used singly or as mixtures as the nitrogen source.

According to the various embodiments of the present invention, phosphoric acid, potassium dihydrogen phosphate or dipotassium hydrogen phosphate or the corresponding sodium-containing salts may be used as the phosphorous source.

The culture medium may additionally comprise salts for example in the form of chlorides or sulfates of metals such as, for example, sodium, potassium, magnesium, calcium and iron, such as, for example, magnesium sulfate or iron sulfate, which are necessary for growth. Finally, essential growth factors such as amino acids, for example homoserine and vitamins, for example thiamine, biotin or pantothenic acid, may be employed in addition to the abovementioned substances.

Starting materials may be added to the culture in the form of a single batch or be fed in during the cultivation in a suitable manner.

To control the pH of the culture, basic compounds such as sodium hydroxide, potassium hydroxide, ammonia or aqueous ammonia, or acidic compounds such as phosphoric acid or sulphuric acid may be employed in a suitable manner. The pH may be adjusted to a value of from 6.0 to 8.5, preferably 6.5 to 8. To control foaming, it may be possible to employ antifoams such as, for example, fatty acid polyglycol esters. To maintain the stability of plasmids, suitable selectively acting substances such as, for example, antibiotics may be added to the medium. In order to maintain aerobic conditions, oxygen or oxygen-containing gas mixtures such as, for example, air may be introduced into the culture. In alternative embodiments, liquids enriched with hydrogen peroxide may be used. The fermentation may be subjected to excess pressure, for example, an excess pressure of from 0.03 to 0.2 MPa. The temperature of the culture may normally be 20° C. to 45° C. and preferably 25° C. to 40° C., particularly preferably 30° to 37° C. In batch processes, the cultivation may be continued until a maximum of the desired L-amino acid has formed, which may normally be achieved within a time range of 10 hours to 160 hours. In continuous processes, longer cultivation times may be possible. The activity of the bacteria may result in an enrichment (accumulation) of the L-amino acid in the fermentation medium and/or in the bacterial cells.

Examples of suitable fermentation media may be found inter alia in the patents U.S. Pat. No. 5,770,409, U.S. Pat. No. 5,840,551 and U.S. Pat. No. 5,990,350 or U.S. Pat. No. 5,275,940.

Analysis of L-amino acids to determine the concentration at one or more time(s) during the fermentation may be accomplished by separating the L-amino acids by ion exchange chromatography, preferably cation exchange chromatography, with subsequent post-column derivatization using ninhydrin, as described by Spackman et al. (Analytical Chemistry 30: 1190-1206 (1958)). It may also be possible to employ ortho-phtaldialdehyde instead of ninhydrin for the post-column derivatization. A review article on ion exchange chromatography may be found in Pickering (LC•GC (Magazine of Chromatographic Science) 7(6), 484-487 (1989)).

It may likewise be possible to carry out a pre-column derivatization for example using ortho-phtaldialdehyde or phenyl isothiocyanate, and to fractionate the resulting amino acid derivatives by reversed phase chromatography (RP), preferably in the form of high performance liquid chromatography (HPLC). A method of this type is described for example in Lindroth et al. (Analytical Chemistry 51: 1167-1174 (1979)). Detection may take place by photometry (absorption, fluorescence).

A summary description of amino acid analysis is to be found inter alia in the textbook "Bioanalytik" by Lottspeich and Zorbas (Spektrum Akademischer Verlag, Heidelberg, Germany 1998).

In various alternative embodiments, the present invention provides a process for preparing L-amino acids, preferably L-lysine, L-glutamic acid, L-glutamine, L-arginine, L-proline or L-ornithine, particularly preferably L-lysine, comprising:
a) fermentation of the cornyeform bacteria according to the invention, preferably of the genus *Corynebacterium*, particularly preferably of the species *Corynebacterium glutamicum*, in a suitable nutrient medium, and
b) accumulation of the L-amino acid in the nutrient medium and/or in the cells of said bacteria.

The process of the present invention may further comprise the provision or preparation or isolation of an L-amino acid-containing product in liquid or solid form.

The fermentation process according to the present invention produces a fermentation broth which comprises the desired L-amino acid.

A fermentation broth according to the present invention may be a fermentation medium or nutrient medium in which a microorganism has been cultivated for a certain time and at a certain temperature. The fermentation medium or the media employed during the fermentation comprise(s) all the substances or components which ensure growth of the microorganism and production of the desired L-amino acid.

When the fermentation according to the present invention is complete, the resulting fermentation broth accordingly comprises
a) the biomass of the microorganism which has been produced as a result of the growth of the cells of the microorganism,
b) the L-amino acid produced during the fermentation,
c) the organic byproducts produced during the fermentation, and
d) the constituents of the fermentation medium employed or of the starting materials such as, for example, vitamins such as biotin or salts such as magnesium sulfate, which have not been consumed by the fermentation.

The organic byproducts may include substances which are produced by the microorganisms employed in the fermentation in addition to the respective L-amino acid and may include sugars such as, for example, trehalose.

The fermentation broth obtained according to the present invention may be removed from the culture vessel or fermentation tank, collected, and used to provide an L-amino acid-containing product in liquid or solid form. The expression "obtaining the L-amino acid-containing product" may also be used to describe this removal, collection and provision of the L-amino acid-containing product. In a simplest case, the L-amino acid-containing fermentation broth itself may be the obtained product.

Alternative embodiments of the present invention may include one or more of the following procedures may be employed to concentrate and/or purify the L-amino acid product:
a) partial (>0% to <80%) to complete (100%) or virtually complete (≥80%, ≥90%, ≥95%, ≥96%, ≥97%, ≥98%, ≥99%) removal of the water,
b) partial (>0% to <80%) to complete (100%) or almost complete (≥80%, ≥90%, ≥95%, ≥96%, ≥97%, ≥98%, ≥99%) removal of the biomass, the latter being optionally inactivated before removal,
c) partial (>0% to <80%) to complete (100%) or virtually complete (≥80%, ≥90%, ≥95%, ≥96%, ≥97%, ≥98%, ≥99%, ≥99.3%, ≥99.7%) removal of the organic byproducts formed during the fermentation, and
d) partial (>0%) to complete (100%) or virtually complete (≥80%, ≥90%, ≥95%, ≥96%, ≥97%, ≥98%, ≥99%, ≥99.3%, ≥99.7%) removal of the constituents of the fermentation medium employed or of the starting materials which have not been consumed by the fermentation.

Products having a specified content of L-amino acid may be obtained by the described procedures.

The partial (>0% to <80%) to complete (100%) or virtually complete (≥80% to <100%) removal of the water (a) may be referred to as drying.

Complete or virtually complete removal of the water, of the biomass, of the organic byproducts and of the unconsumed constituents of the fermentation medium obtained according to the present invention provides pure (≥80% by weight, ≥90% by weight) or high-purity (≥95% by weight, ≥97% by weight, ≥99% by weight) product forms of the L-amino acids. Technical instructions for the procedures a), b), c) or d) are conventionally available and known to skilled artisans.

Four different product forms of the amino acid L-lysine, are conventionally known.

One form of L-lysine-containing products includes concentrated aqueous alkaline solutions of purified L-lysine (EP-B-0534865). A further form, as described for example in U.S. Pat. No. 6,340,486 and U.S. Pat. No. 6,465,025, includes aqueous acidic biomass-containing concentrates of L-lysine-containing fermentation broths. Solid forms include powders or crystalline forms of purified or pure L-lysine, which may typically be in the form of a salt such as, for example, L-lysine monohydrochloride. A further solid product form is described for example in EP-B-0533039. The product form described therein comprises besides L-lysine most of the starting materials used during the fermentative production and not consumed and, where appropriate, the biomass of the microorganism employed with a proportion of L-lysine ranging from greater than 0% to 100% by weight.

A wide variety of processes appropriate for the various product forms are known to one of ordinary skill in the art for producing the L-lysine-containing product or the purified L-lysine from the fermentation broth.

Methods to produce pure solid L-lysine include ion exchange chromatography, with optional use of activated carbon and crystallization. The corresponding base or a corresponding salt such as, for example, the monohydrochloride (Lys-HCl) or lysine sulfate (Lys$_2$-H$_2$SO$_4$) may be obtained by this method.

EP-B-0534865 describes a process for producing aqueous basic L-lysine-containing solutions from fermentation broths. In the process described therein, the biomass is separated from the fermentation broth and discarded. A base such as, for example, sodium, potassium or ammonium hydroxide is used to adjust the broth to a pH of between 9 to 11. The mineral constituents (inorganic salts) are removed from the broth by crystallization after concentration and cooling, and are either used as fertilizer or discarded.

In processes for producing lysine by using the bacteria according to the present invention, preferred processes are those resulting in products which comprise constituents of the fermentation broth. These may be used in particular as animal feed additives.

Depending on requirements specified for the product, the biomass may be removed wholly or partly from the fermentation broth by separation methods such as, for example, centrifugation, filtration, decantation or a combination thereof, or be left completely therein. Optionally, the biomass or the biomass-containing fermentation broth may be inactivated during a suitable process step, for example by thermal treatment (heating) or by addition of acid.

In alternative embodiments of the present invention, the biomass may be completely or virtually completely removed so that no (0%) or at most 30%, at most 20%, at most 10%, at most 5%, at most 1% or at most 0.1% biomass remains in the prepared product. In further embodiments, the biomass is not removed, or is removed only in small proportions, so that all (100%) or more than 70%, 80%, 90%, 95%, 99% or 99.9% biomass remains in the product prepared. In an embodiment according to the present invention, accordingly, the biomass may be removed in proportions of from ≥0% to ≤100%.

The fermentation broth obtained according to the present invention after the fermentation, may be adjusted, before or after the complete or partial removal of the biomass, to an acidic pH with an inorganic acid such as, for example, hydrochloric acid, sulfuric acid or phosphoric acid or organic acids such as, for example, propionic acid (GB 1,439,728 or EP 1 331 220). It may also be possible to acidify the fermentation broth with the complete content of biomass. In another embodiment, the broth may also be stabilized by adding sodium bisulfite ($NaHSO_3$, GB 1,439,728) or another salt, for example an ammonium, alkali metal or alkaline earth metal salt of sulfurous acid.

During the removal of the biomass, organic or inorganic solids present in the fermentation broth may be optionally partially or completely removed. The organic byproducts dissolved in the fermentation broth, and the dissolved unconsumed constituents of the fermentation medium (starting materials) may remain at least partly (>0%), preferably to the extent of at least 25%, particularly preferably to the extent of at least 50% and very particularly preferably to the extent of at least 75% in the product. Optionally, the organic byproducts dissolved in the fermentation broth, and the dissolved unconsumed constituents of the fermentation medium may also remain completely (100%) or virtually completely, meaning >95% or >98% or greater than 99%, in the product. If a product in this sense comprises at least part of the constituents of the fermentation broth, this may also be described by the term "product based on fermentation broth".

Subsequently, water may be removed from the broth, or the fermentation broth thickened or concentrated, by known methods such as, for example, using a rotary evaporator, thin-film evaporator, falling-film evaporator, by reverse osmosis or by nanofiltration. The concentrated fermentation broth may then be worked up to free-flowing products, in particular to a fine-particle powder or preferably coarse granules, by methods of freeze drying, spray drying, spray granulation or by other processes as described for example in the circulating fluidized bed according to PCT/EP2004/006655. A desired product may optionally be isolated from the resulting granules by screening or dust removal.

It may also be possible to dry the fermentation broth directly, i.e. without previous concentration by spray drying or spray granulation.

"Free-flowing" is used to describe powders which flow unimpeded out of a series of glass orifice vessels with orifices of different sizes, at least out of the vessel with a 5 mm (millimeters) orifice (Klein: Seifen, Öle, Fette, Wachse 94, 12 (1968)). "Fine-particle" describes a powder predominantly (>50%) having a particle size of diameter from 20 to 200 µm. "Coarse" describes a product predominantly (>50%) of a particle size of diameter from 200 to 2000 µm.

The particle size determination may be obtained by methods of laser diffraction spectrometry. Corresponding methods are described in the textbook on "Teilchengrößenmessung in der Laborpraxis" by R. H. Müller and R. Schuhmann, Wissenschaftliche Verlagsgesellschaft Stuttgart (1996) or in the textbook "Introduction to Particle Technology" by M. Rhodes, published by Wiley & Sons (1998).

The free-flowing, fine-particle powder may be converted by suitable compaction or granulation processes into a coarse, very free-flowing, storable and substantially dust-free product.

The term "dust-free" describes that the product comprises only small proportions (<5%) of particle sizes below 100 µm in diameter.

"Storable" in the sense of the present invention describes a product which can be stored for at least one (1) year or longer, preferably at least 1.5 years or longer, particularly preferably two (2) years or longer, in a dry and cool environment without any substantial loss (at most 5%) of the respective amino acid occurring.

In a further embodiment, the present invention includes a process, which is described in principle in DE 102006016158, and in which the fermentation broth obtained using the microorganisms according to the present invention, from which the biomass has been optionally removed completely or partially, may be further processed according to the following:

the pH is reduced by adding sulfuric acid to 4.0 to 5.2, in particular 4.9 to 5.1, and a molar sulfate/L-lysine ratio of from 0.85 to 1.2, preferably 0.9 to 1.0, particularly preferably >0.9 to <0.95, is adjusted in the broth, optionally by adding a further or a plurality of sulfate-containing compound(s), and
a) the mixture obtained in this way is concentrated by removal of water, and optionally granulated,
where one or both of the following is/are optionally carried out before a):
c) measurement of the molar sulfate/L-lysine ratio to ascertain the required amount of sulfate-containing compound(s);
d) addition of a sulfate-containing compound selected from the group of ammonium sulfate, ammonium bisulfate and sulfuric acid in appropriate ratios.

Optionally also before b), a salt of sulfurous acid, preferably alkali metal bisulfite, particularly preferably sodium bisulfite, may be added in a concentration of from 0.01 to 0.5% by weight, preferably 0.1 to 0.3% by weight, particularly preferably 0.1 to 0.2% by weight, based on the fermentation broth. Preferred sulfate-containing compounds for the abovementioned procedures may include ammonium sulfate and/or ammonium bisulfate or mixtures of ammonia and sulfuric acid and sulfuric acid itself.

The molar sulfate/L-lysine ratio V may be calculated by the formula:

$$V = 2 \times [SO_4^{2-}]/[\text{L-lysine}].$$

This formula takes account of the fact that the $SO_4^{2-}$ anion is doubly charged, or sulfuric acid is dibasic. A ratio of V=1 indicates that the stoichiometric composition $Lys_2H_2(SO_4)$ is present, whereas a ratio of V=0.9 indicates a 10% sulfate deficient composition and a ratio of V=1.1 indicates a 10% sulfate excess composition.

It may be advantageous to employ the usual organic or inorganic auxiliaries or carriers such as starch, gelatin, cellulose derivatives or similar substances, as normally used in the processing of food products or feeds as binders, gelling agents or thickeners, or further substances such as, for example, silicas, silicates (EP0743016A) or stearates during the granulation or compaction of the compositions obtained according to the present invention.

It may be further advantageous to provide the surface of the resulting granules with oils as described in WO 04/054381. Oils which may be used, include mineral oils, vegetable oils or mixtures of vegetable oils. Examples of such oils are soybean oil, olive oil, soybean oil/lecithin mixtures. In the same way, silicone oils, polyethylene glycols or hydroxyethylcellulose are also suitable. Treatment of the surfaces of the granules with oils increases the abrasion resistance of the product granule and may provide a reduction in the dust content. The oil content in the product may be from 0.02 to 2.0% by weight, preferably 0.02 to 1.0% by weight, and very particularly preferably 0.2 to 1.0% by weight, based on the total amount of the feed additive.

Preferred products have a proportion of ≥97% by weight with a particle size of from 100 to 1800 μm or a proportion of ≥95% by weight with a particle size of 300 to 1800 μm diameter. The proportion of dust, i.e. particles with a particle size <100 μm, is preferably less than 1% by weight, particularly preferably not exceeding 0.5% by weight.

Alternatively, the product according to the present invention may be absorbed on an organic or inorganic carrier conventionally known for the processing of feeds, such as, for example, silicas, silicates, meals, brans, flours, starches, sugars or others, and/or be mixed and stabilized with conventional thickeners or binders. Examples of use and processes therefore are described in Die Mühle+Mischfuttertechnik, 132 (1995) 49, page 817.

In a further alternative embodiment, the product of the present invention may be made stable to digestion by animal stomachs, especially the stomach of ruminants by coating the granules with film-formers such as, for example, metal carbonates, silicas, silicates, alginates, stearates, starches, gums and cellulose ethers, as described in DE-C-4100920.

To adjust a desired L-lysine concentration in the product it may be possible, depending on requirements, to add L-lysine during the process in the form of a concentrate or, where appropriate, of a substantially pure substance or its salt in liquid or solid form. These can be added singly or as mixtures to the resulting or concentrated fermentation broth, or else during the drying or granulation process.

One embodiment of the present invention further includes a process for producing a solid L-lysine-containing product, according to description in US 20050220933, and which includes a working up method of the fermentation broth obtained using the microorganisms according to the present invention, the working up method comprising:

a) filtration of the fermentation broth, preferably with a membrane filter, to obtain a biomass-containing slurry and a filtrate,
b) concentration of the filtrate, preferably so as to result in a solids content of from 48 to 52% by weight,
c) granulation of the concentrate obtained in b), preferably at a temperature of from 50° C. to 62° C., and
d) coating of the granules obtained in c), with one or more of the coating agent(s). The coating agents preferably used for the coating in d) are selected from the group consisting of
d1) the biomass obtained in a),
d2) a L-lysine-containing compound, preferably selected from the group of L-lysine hydrochloride or L-lysine sulfate,
d3) a L-lysine-free substance with an L-lysine content of <1% by weight, preferably <0.5% by weight, preferably selected from the group of starch, carrageenan, agar, silicas, silicates, meals, brans and flours, and
d4) a water-repellent substance, preferably selected from the group of oils, polyethylene glycols and liquid paraffins.

The L-lysine content may be adjusted to a specific value by employing one or more of d1) to d4), in particular d1) to d3).

In one preferred embodiment of the present invention the molar ion ratio of the L-lysine-containing products, may be adjusted so that the molar ion ratio described by the formula $$2\times[SO_4^{2-}]+[Cl^-]-[NH_4^+]-[Na^+]-[K^+]-2\times[Mg^{2+}]-2\times[Ca^{2+}]/[L\text{-}Lys]$$

is from 0.68 to 0.95, preferably 0.68 to 0.90, particularly preferably 0.68 to 0.86, as described by Kushiki et al. in US 20030152633.

In the case of L-lysine according to the present invention, the solid product according to alternative embodiments comprises a lysine content (as lysine base) of from 10% by weight to 70% by weight or 20% by weight to 70% by weight, preferably 30% by weight to 70% by weight and very particularly preferably from 40% by weight to 70% by weight, based on the dry matter of the product. Maximum lysine base contents may be 71% by weight, 72% by weight, or 73% by weight. The water content of the L-lysine-containing solid product may be up to 5% by weight, preferably up to 4% by weight, and particularly preferably less than 3% by weight.

The invention claimed is:

1. An isolated polynucleotide comprising the promoter region of the amtR gene shown in SEQ ID NO:5 and wherein the amtR gene is attenuated by at least one of
   a) replacement of the guanine at position 7 of SEQ ID NO:5 by thymine,
   b) replacement of cytosine at position 11 of SEQ ID NO:5 by guanine,
   c) replacement of thymine at position 40 of SEQ ID NO:5 by guanine,
   d) replacement of thymine at position 45 of SEQ ID NO:5 by guanine,
   e) deletion of one or more of the nucleobases of position 40 to 45 of SEQ ID NO:5,
   f) deletion of one or more of the nucleobases between position 72 and 78 of SEQ ID NO:5, and
   g) replacement of one or more of the nucleobases adenine or guanine between position 72 and 78 of SEQ ID NO:5 by thymine or cytosine.

2. A vector comprising a polynucleotide as claimed in claim 1.

3. An isolated microorganism cell comprising the vector as claimed in claim 2.

4. An isolated microorganism cell comprising the polynucleotide as claimed in claim 1.

5. The isolated polynucleotide of claim 1, wherein the amtR gene is attenuated by replacement of the guanine at position 7 of SEQ ID NO:5 by thymine.

6. The isolated polynucleotide of claim 1, wherein the amtR gene is attenuated by replacement of cytosine at position 11 of SEQ ID NO:5 by guanine.

7. The isolated polynucleotide of claim 1, wherein the amtR gene is attenuated by replacement of thymine at position 40 of SEQ ID NO:5 by guanine.

8. The isolated polynucleotide of claim 1, wherein the amtR gene is attenuated by replacement of thymine at position 45 of SEQ ID NO:5 by guanine.

9. The isolated polynucleotide of claim 1, wherein the amtR gene is attenuated by deletion of one or more of the nucleobases of position 40 to 45 of SEQ ID NO:5.

10. The isolated polynucleotide of claim 1, wherein the amtR gene is attenuated by deletion of all nucleobases of position 40 to 45 of SEQ ID NO:5.

11. The isolated polynucleotide of claim 1, wherein the amtR gene is attenuated by deletion of one or more of the nucleobases between position 72 and 78 of SEQ ID NO:5.

12. The isolated polynucleotide of claim 1, wherein the amtR gene is attenuated by replacement of one or more of the nucleobases adenine or guanine between position 72 and 78 of SEQ ID NO:5 by thymine or cytosine.

* * * * *

SEQUENCE LISTING

```
<160> NUMBER OF SEQ ID NOS: 25

<210> SEQ ID NO 1
<211> LENGTH: 669
<212> TYPE: DNA
<213> ORGANISM: Corynebacterium glutamicum
<220> FEATURE:
<223> OTHER INFORMATION: Corynebacterium glutamicum ATCC13032
<220> FEATURE:
<221> NAME/KEY: CDS
<222> LOCATION: (1)..(666)
<223> OTHER INFORMATION: amtR gene
<220> FEATURE:
<221> NAME/KEY: misc_feature
<222> LOCATION: (8)..(8)
<223> OTHER INFORMATION: Nucleobase G

<400> SEQUENCE: 1 atg gca gga gca gtg gga cgc ccc cgg aga tca gct ccg cga cgg gca      48
Met Ala Gly Ala Val Gly Arg Pro Arg Arg Ser Ala Pro Arg Arg Ala
1               5                   10                  15
```

```
ggc aag aat cct cgc gag gag att ctt gac gcc tct gct gag ctt ttc        96
Gly Lys Asn Pro Arg Glu Glu Ile Leu Asp Ala Ser Ala Glu Leu Phe
         20                  25                  30 acc cgt caa ggc ttc gca aca acc tcc acg cat caa atc gct gat gcc       144
Thr Arg Gln Gly Phe Ala Thr Thr Ser Thr His Gln Ile Ala Asp Ala
     35                  40                  45 gtg gga atc cgc caa gcc tcg ctg tat tat cac ttc ccg tcc aag acg       192
Val Gly Ile Arg Gln Ala Ser Leu Tyr Tyr His Phe Pro Ser Lys Thr
 50                  55                  60 gaa atc ttc ctc acc ctg ctg aaa tct act gtc gag ccg tcc act gtg       240
Glu Ile Phe Leu Thr Leu Leu Lys Ser Thr Val Glu Pro Ser Thr Val
 65                  70                  75                  80 ctc gcc gaa gac tta agc acc ctg gac gcc gga cct gag atg cgc ctc       288
Leu Ala Glu Asp Leu Ser Thr Leu Asp Ala Gly Pro Glu Met Arg Leu
                 85                  90                  95 tgg gca atc gtt gcc tcc gaa gtg cgt ctg ctg tcc acc aag tgg           336
Trp Ala Ile Val Ala Ser Glu Val Arg Leu Leu Ser Thr Lys Trp
            100                 105                 110 aac gtc ggt cgc ctg tac caa ctc ccc atc gtt ggt tct gaa gag ttc       384
Asn Val Gly Arg Leu Tyr Gln Leu Pro Ile Val Gly Ser Glu Glu Phe
        115                 120                 125 gcc gag tac cac agc cag cgc gaa gcc ctc acc aac gtc ttc cgc gac       432
Ala Glu Tyr His Ser Gln Arg Glu Ala Leu Thr Asn Val Phe Arg Asp
    130                 135                 140 ctc gcc acc gaa atc gtc ggt gac gac ccc cgc gca gaa ctc ccc ttc       480
Leu Ala Thr Glu Ile Val Gly Asp Asp Pro Arg Ala Glu Leu Pro Phe
145                 150                 155                 160 cac atc acc atg tcg gtg atc gaa atg cgt cgc aac gac ggc aag att       528
His Ile Thr Met Ser Val Ile Glu Met Arg Arg Asn Asp Gly Lys Ile
                165                 170                 175 cca agc ccg ctt tcc gca gac agc ctc ccg gag acc gca att atg ctt       576
Pro Ser Pro Leu Ser Ala Asp Ser Leu Pro Glu Thr Ala Ile Met Leu
            180                 185                 190 gcc gac gcc tcc ctc gcc gtc ctc ggc gcg ccg ctg ccc gcc gac cgg       624
Ala Asp Ala Ser Leu Ala Val Leu Gly Ala Pro Leu Pro Ala Asp Arg
        195                 200                 205 gtc gaa aaa acg ctt gaa cta atc aag cag gct gac gcg aaa taa           669
Val Glu Lys Thr Leu Glu Leu Ile Lys Gln Ala Asp Ala Lys
    210                 215                 220

<210> SEQ ID NO 2
<211> LENGTH: 222
<212> TYPE: PRT
<213> ORGANISM: Corynebacterium glutamicum
<220> FEATURE:
<223> OTHER INFORMATION: Corynebacterium glutamicum ATCC13032

<400> SEQUENCE: 2

Met Ala Gly Ala Val Gly Arg Pro Arg Arg Ser Ala Pro Arg Arg Ala
 1               5                  10                  15

Gly Lys Asn Pro Arg Glu Glu Ile Leu Asp Ala Ser Ala Glu Leu Phe
             20                  25                  30

Thr Arg Gln Gly Phe Ala Thr Thr Ser Thr His Gln Ile Ala Asp Ala
         35                  40                  45

Val Gly Ile Arg Gln Ala Ser Leu Tyr Tyr His Phe Pro Ser Lys Thr
     50                  55                  60

Glu Ile Phe Leu Thr Leu Leu Lys Ser Thr Val Glu Pro Ser Thr Val
 65                  70                  75                  80

Leu Ala Glu Asp Leu Ser Thr Leu Asp Ala Gly Pro Glu Met Arg Leu
                 85                  90                  95
```

```
Trp Ala Ile Val Ala Ser Glu Val Arg Leu Leu Ser Thr Lys Trp
            100                 105                 110

Asn Val Gly Arg Leu Tyr Gln Leu Pro Ile Val Gly Ser Glu Phe
        115                 120                 125

Ala Glu Tyr His Ser Gln Arg Glu Ala Leu Thr Asn Val Phe Arg Asp
130                 135                 140

Leu Ala Thr Glu Ile Val Gly Asp Asp Pro Arg Ala Glu Leu Pro Phe
145                 150                 155                 160

His Ile Thr Met Ser Val Ile Glu Met Arg Arg Asn Asp Gly Lys Ile
                165                 170                 175

Pro Ser Pro Leu Ser Ala Asp Ser Leu Pro Glu Thr Ala Ile Met Leu
            180                 185                 190

Ala Asp Ala Ser Leu Ala Val Leu Gly Ala Pro Leu Pro Ala Asp Arg
        195                 200                 205

Val Glu Lys Thr Leu Glu Leu Ile Lys Gln Ala Asp Ala Lys
    210                 215                 220

<210> SEQ ID NO 3
<211> LENGTH: 2669
<212> TYPE: DNA
<213> ORGANISM: Corynebacterium glutamicum
<220> FEATURE:
<223> OTHER INFORMATION: Corynebacterium glutamicum ATCC13032
<220> FEATURE:
<221> NAME/KEY: misc_feature
<222> LOCATION: (1)..(1000)
<223> OTHER INFORMATION: Sequence located upstream of the coding region
<220> FEATURE:
<221> NAME/KEY: CDS
<222> LOCATION: (1001)..(1666)
<223> OTHER INFORMATION: amtR gene
<220> FEATURE:
<221> NAME/KEY: misc_feature
<222> LOCATION: (1008)..(1008)
<223> OTHER INFORMATION: Nucleobase G
<220> FEATURE:
<221> NAME/KEY: misc_feature
<222> LOCATION: (1667)..(2669)
<223> OTHER INFORMATION: Sequence located downstream of the coding
      region

<400> SEQUENCE: 3
ctatgtctga ttctattggt gtcgcatgcg cagtgtagtt ttagaactac tagagaactg      60
gaaggaatca ctcgtgcttc acccctcatt gactgagcta gcggatgctg ccccacttgc     120
acaggatttt gccaccgtcc gcggtgtgct gaaggaatcg ctggatttgt tgggcaatgc     180
actgaaccac ggtgaagagc ccgcggagct tgcagggtgg ctgtcacaag ttattactga     240
tgttttgcac tcccctggct tggatgccca cgtggtgctc accggccccg tggggcgtgg     300
agacgcactg cctacctcgc ccgtgaggtg gctggcggtc gtcgatagcc aagaagatcc     360
gaatgaaaag atttcagcgc tgttaactga ggtgggcttc attgcggagc gatcggtgc     420 ggcaactcgt gaggagtggg agcagcgtgc gcgcgctggt gaggatccag aggtctattt     480
ggatgctggc acgtgggtcg cggcgatcgc tgaagtagat gacaaagcac tgttgcagga     540
tgcgttgtca tctaggccgc ctgcggtgga aacttatgag ggtcttcctt cgttggacat     600
ggtggtaaac attcgtgaga acctcatgat tcccacggtg aagatcgctc gctgggcagc     660
acacaaggct ggttctttgg cgcctacgac tgcgcagcgc ctcgtggatg cccgtggtgt     720
gctcaccaat gatgaagtcg acgcgctgac acaggtgtgg acttccgcac tgagcttgca     780
gtcgaaacgt tggatggatc acatccatga tcaagaaacc accgcttggg agcttcccgc     840
```

```
gctgcaacgt gccactttg gcgcatcggc tcggttgctt tctgaggtgt tgcggtccgt      900
tgaagcccgt gaaatcgata ccaaatagga actctgcaca attactggct acaatctctt      960
gagatcaata ggccaaactt taaggaagta gaattacgct atg gca gga gca gtg     1015
                                              Met Ala Gly Ala Val
                                               1               5 gga cgc ccc cgg aga tca gct ccg cga cgg gca ggc aag aat cct cgc     1063
Gly Arg Pro Arg Arg Ser Ala Pro Arg Arg Ala Gly Lys Asn Pro Arg
             10                  15                  20 gag gag att ctt gac gcc tct gct gag ctt ttc acc cgt caa ggc ttc     1111
Glu Glu Ile Leu Asp Ala Ser Ala Glu Leu Phe Thr Arg Gln Gly Phe
             25                  30                  35 gca aca acc tcc acg cat caa atc gct gat gcc gtg gga atc cgc caa     1159
Ala Thr Thr Ser Thr His Gln Ile Ala Asp Ala Val Gly Ile Arg Gln
 40                  45                  50 gcc tcg ctg tat tat cac ttc ccg tcc aag acg gaa atc ttc ctc acc     1207
Ala Ser Leu Tyr Tyr His Phe Pro Ser Lys Thr Glu Ile Phe Leu Thr
 55                  60                  65 ctg ctg aaa tct act gtc gag ccg tcc act gtg ctc gcc gaa gac tta     1255
Leu Leu Lys Ser Thr Val Glu Pro Ser Thr Val Leu Ala Glu Asp Leu
 70                  75                  80                  85 agc acc ctg gac gcc gga cct gag atg cgc ctc tgg gca atc gtt gcc     1303
Ser Thr Leu Asp Ala Gly Pro Glu Met Arg Leu Trp Ala Ile Val Ala
                 90                  95                 100 tcc gaa gtg cgt ctg ctg ctg tcc acc aag tgg aac gtc ggt cgc ctg     1351
Ser Glu Val Arg Leu Leu Leu Ser Thr Lys Trp Asn Val Gly Arg Leu
                105                 110                 115 tac caa ctc ccc atc gtt ggt tct gaa gag ttc gcc gag tac cac agc     1399
Tyr Gln Leu Pro Ile Val Gly Ser Glu Glu Phe Ala Glu Tyr His Ser
                120                 125                 130 cag cgc gaa gcc ctc acc aac gtc ttc cgc gac ctc gcc acc gaa atc     1447
Gln Arg Glu Ala Leu Thr Asn Val Phe Arg Asp Leu Ala Thr Glu Ile
            135                 140                 145 gtc ggt gac gac ccc cgc gca gaa ctc ccc ttc cac atc acc atg tcg     1495
Val Gly Asp Asp Pro Arg Ala Glu Leu Pro Phe His Ile Thr Met Ser
150                 155                 160                 165 gtg atc gaa atg cgt cgc aac gac ggc aag att cca agc ccg ctt tcc     1543
Val Ile Glu Met Arg Arg Asn Asp Gly Lys Ile Pro Ser Pro Leu Ser
                170                 175                 180 gca gac agc ctc ccg gag acc gca att atg ctt gcc gac gcc tcc ctc     1591
Ala Asp Ser Leu Pro Glu Thr Ala Ile Met Leu Ala Asp Ala Ser Leu
                185                 190                 195 gcc gtc ctc ggc gcg ccg ctg ccc gcc gac cgg gtc gaa aaa acg ctt     1639
Ala Val Leu Gly Ala Pro Leu Pro Ala Asp Arg Val Glu Lys Thr Leu
                200                 205                 210 gaa cta atc aag cag gct gac gcg aaa taaccatccg cgcctgcgaa           1686
Glu Leu Ile Lys Gln Ala Asp Ala Lys
            215                 220 atcaacggag catcaatcat ctgaccatcc agtttgaacg cacctggatg gtttttctgct   1746 tcctccacca ctttcttcgc ccactccaac tggttagcct ctggccgata ggctctccga   1806
acaatctcga tctgcttggg gtgaatgcat gcggtgccag cgaaaccagt ccgcgcagca   1866
tcgaccgctt ctaaatagag gccctcttca tcgtggaaat ccgcatggat ggcatcaatg   1926
gtgaacttcc cattcgccgc cgcgtggagg tgcatcaggg cgcgtgtaag cctcatggtg   1986
tctcggtagg agccttcatt ggactcatca cccaagaacc tagaatgagt gcctcccaag   2046
aggtgtgtga gatcctccgc gccccagaac attccaacga ctttagggtc cgcagcaatc   2106
```

```
tgaggaatgc tggttgcagc ctgaggggtt tcaatcatgg cgataatgtt gaggccatct   2166
aattcctcag gcacgctgcc aagaagttta ggaaccataa caagtgtgaa atccgtggac   2226
ttcaccatct ccacgtcagc caaaaagtgt ggatcgctcg ccctacggt tctcacaatg    2286 gttcgtttag gatccaaccc cgattctcta atgttcctgt aggcgacctc acggtctacc   2346
tcccctgccc catcttccaa atcaatgatg accatatcgg ccttcgatgc tgcttttgga   2406
atgatctcag cacgtccagc tggtgcgaag agaatagctg gtccacaaat aagttcagac   2466
atgtactcat taatacgcga aaaggcagac cttatggtct gccttcaagc gaaatcttta   2526
aaaactttag tgagcgaagt gtcgcgcacc agtcaggtac atggtcacgc cagccttgtt   2586
ggctgcctca atgacctcgt tgtcgcgaat ggatccacca ggctgcacaa cagcagtgat   2646
gccagcctca gcgagaacct caa                                           2669
```

<210> SEQ ID NO 4
<211> LENGTH: 222
<212> TYPE: PRT
<213> ORGANISM: Corynebacterium glutamicum
<220> FEATURE:
<223> OTHER INFORMATION: Corynebacterium glutamicum ATCC13032

<400> SEQUENCE: 4

```
Met Ala Gly Ala Val Gly Arg Pro Arg Arg Ser Ala Pro Arg Arg Ala
1               5                   10                  15

Gly Lys Asn Pro Arg Glu Glu Ile Leu Asp Ala Ser Ala Glu Leu Phe
            20                  25                  30

Thr Arg Gln Gly Phe Ala Thr Thr Ser Thr His Gln Ile Ala Asp Ala
        35                  40                  45

Val Gly Ile Arg Gln Ala Ser Leu Tyr Tyr His Phe Pro Ser Lys Thr
    50                  55                  60

Glu Ile Phe Leu Thr Leu Leu Lys Ser Thr Val Gly Pro Ser Thr Val
65                  70                  75                  80

Leu Ala Glu Asp Leu Ser Thr Leu Asp Ala Gly Pro Glu Met Arg Leu
                85                  90                  95

Trp Ala Ile Val Ala Ser Glu Val Arg Leu Leu Leu Ser Thr Lys Trp
            100                 105                 110

Asn Val Gly Arg Leu Tyr Gln Leu Pro Ile Val Gly Ser Glu Glu Phe
        115                 120                 125

Ala Glu Tyr His Ser Gln Arg Glu Ala Leu Thr Asn Val Phe Arg Asp
    130                 135                 140

Leu Ala Thr Glu Ile Val Gly Asp Pro Arg Ala Glu Leu Pro Phe
145                 150                 155                 160

His Ile Thr Met Ser Val Ile Glu Met Arg Arg Asn Asp Gly Lys Ile
                165                 170                 175

Pro Ser Pro Leu Ser Ala Asp Ser Leu Pro Glu Thr Ala Ile Met Leu
            180                 185                 190

Ala Asp Ala Ser Leu Ala Val Leu Gly Ala Pro Leu Pro Ala Asp Arg
        195                 200                 205

Val Glu Lys Thr Leu Glu Leu Ile Lys Gln Ala Asp Ala Lys
    210                 215                 220
```

<210> SEQ ID NO 5
<211> LENGTH: 90
<212> TYPE: DNA
<213> ORGANISM: Corynebacterium glutamicum

<400> SEQUENCE: 5

```
gaaatcgata ccaaatagga actctgcaca attactggct acaatctctt gagatcaata      60
ggccaaactt taaggaagta gaattacgct                                       90

<210> SEQ ID NO 6
<211> LENGTH: 669
<212> TYPE: DNA
<213> ORGANISM: Corynebacterium glutamicum
<220> FEATURE:
<221> NAME/KEY: CDS
<222> LOCATION: (1)..(666)
<223> OTHER INFORMATION: amtR allele
<220> FEATURE:
<221> NAME/KEY: mutation
<222> LOCATION: (8)..(8)
<223> OTHER INFORMATION: G > A transition

<400> SEQUENCE: 6
```

| | | | | | | | | | | | | | | | | |
|---|---|---|---|---|---|---|---|---|---|---|---|---|---|---|---|---|
| atg | gca | gaa | gca | gtg | gga | cgc | ccc | cgg | aga | tca | gct | ccg | cga | cgg | gca | 48 |
| Met | Ala | Glu | Ala | Val | Gly | Arg | Pro | Arg | Arg | Ser | Ala | Pro | Arg | Arg | Ala | |
| 1 | | | | 5 | | | | | 10 | | | | | 15 | | |
| ggc | aag | aat | cct | cgc | gag | gag | att | ctt | gac | gcc | tct | gct | gag | ctt | ttc | 96 |
| Gly | Lys | Asn | Pro | Arg | Glu | Glu | Ile | Leu | Asp | Ala | Ser | Ala | Glu | Leu | Phe | |
| | | | 20 | | | | | 25 | | | | | 30 | | | |
| acc | cgt | caa | ggc | ttc | gca | aca | acc | tcc | acg | cat | caa | atc | gct | gat | gcc | 144 |
| Thr | Arg | Gln | Gly | Phe | Ala | Thr | Thr | Ser | Thr | His | Gln | Ile | Ala | Asp | Ala | |
| | | 35 | | | | | 40 | | | | | 45 | | | | |
| gtg | gga | atc | cgc | caa | gcc | tcg | ctg | tat | tat | cac | ttc | ccg | tcc | aag | acg | 192 |
| Val | Gly | Ile | Arg | Gln | Ala | Ser | Leu | Tyr | Tyr | His | Phe | Pro | Ser | Lys | Thr | |
| | 50 | | | | | 55 | | | | | 60 | | | | | |
| gaa | atc | ttc | ctc | acc | ctg | ctg | aaa | tct | act | gtc | gag | ccg | tcc | act | gtg | 240 |
| Glu | Ile | Phe | Leu | Thr | Leu | Leu | Lys | Ser | Thr | Val | Glu | Pro | Ser | Thr | Val | |
| 65 | | | | | 70 | | | | | 75 | | | | | 80 | |
| ctc | gcc | gaa | gac | tta | agc | acc | ctg | gac | gcc | gga | cct | gag | atg | cgc | ctc | 288 |
| Leu | Ala | Glu | Asp | Leu | Ser | Thr | Leu | Asp | Ala | Gly | Pro | Glu | Met | Arg | Leu | |
| | | | | 85 | | | | | 90 | | | | | 95 | | |
| tgg | gca | atc | gtt | gcc | tcc | gaa | gtg | cgt | ctg | ctg | ctg | tcc | acc | aag | tgg | 336 |
| Trp | Ala | Ile | Val | Ala | Ser | Glu | Val | Arg | Leu | Leu | Leu | Ser | Thr | Lys | Trp | |
| | | | 100 | | | | | 105 | | | | | 110 | | | |
| aac | gtc | ggt | cgc | ctg | tac | caa | ctc | ccc | atc | gtt | ggt | tct | gaa | gag | ttc | 384 |
| Asn | Val | Gly | Arg | Leu | Tyr | Gln | Leu | Pro | Ile | Val | Gly | Ser | Glu | Glu | Phe | |
| | | 115 | | | | | 120 | | | | | 125 | | | | |
| gcc | gag | tac | cac | agc | cag | cgc | gaa | gcc | ctc | acc | aac | gtc | ttc | cgc | gac | 432 |
| Ala | Glu | Tyr | His | Ser | Gln | Arg | Glu | Ala | Leu | Thr | Asn | Val | Phe | Arg | Asp | |
| | 130 | | | | | 135 | | | | | 140 | | | | | |
| ctc | gcc | acc | gaa | atc | gtc | ggt | gac | gac | ccc | cgc | gca | gaa | ctc | ccc | ttc | 480 |
| Leu | Ala | Thr | Glu | Ile | Val | Gly | Asp | Asp | Pro | Arg | Ala | Glu | Leu | Pro | Phe | |
| 145 | | | | | 150 | | | | | 155 | | | | | 160 | |
| cac | atc | acc | atg | tcg | gtg | atc | gaa | atg | cgt | cgc | aac | gac | ggc | aag | att | 528 |
| His | Ile | Thr | Met | Ser | Val | Ile | Glu | Met | Arg | Arg | Asn | Asp | Gly | Lys | Ile | |
| | | | | 165 | | | | | 170 | | | | | 175 | | |
| cca | agc | ccg | ctt | tcc | gca | gac | agc | ctc | ccg | gag | acc | gca | att | atg | ctt | 576 |
| Pro | Ser | Pro | Leu | Ser | Ala | Asp | Ser | Leu | Pro | Glu | Thr | Ala | Ile | Met | Leu | |
| | | | 180 | | | | | 185 | | | | | 190 | | | |
| gcc | gac | gcc | tcc | ctc | gcc | gtc | ctc | ggc | gcg | ccg | ctg | ccc | gcc | gac | cgg | 624 |
| Ala | Asp | Ala | Ser | Leu | Ala | Val | Leu | Gly | Ala | Pro | Leu | Pro | Ala | Asp | Arg | |
| | | 195 | | | | | 200 | | | | | 205 | | | | |
| gtc | gaa | aaa | acg | ctt | gaa | cta | atc | aag | cag | gct | gac | gcg | aaa | taa | | 669 |
| Val | Glu | Lys | Thr | Leu | Glu | Leu | Ile | Lys | Gln | Ala | Asp | Ala | Lys | | | |
| | 210 | | | | | 215 | | | | | 220 | | | | | |

```
<210> SEQ ID NO 7
```

<211> LENGTH: 222
<212> TYPE: PRT
<213> ORGANISM: Corynebacterium glutamicum

<400> SEQUENCE: 7

Met Ala Glu Ala Val Gly Arg Pro Arg Ser Ala Pro Arg Arg Ala
1               5                   10                  15

Gly Lys Asn Pro Arg Glu Glu Ile Leu Asp Ala Ser Ala Glu Leu Phe
            20                  25                  30

Thr Arg Gln Gly Phe Ala Thr Thr Ser Thr His Gln Ile Ala Asp Ala
        35                  40                  45

Val Gly Ile Arg Gln Ala Ser Leu Tyr Tyr His Phe Pro Ser Lys Thr
    50                  55                  60

Glu Ile Phe Leu Thr Leu Leu Lys Ser Thr Val Glu Pro Ser Thr Val
65                  70                  75                  80

Leu Ala Glu Asp Leu Ser Thr Leu Asp Ala Gly Pro Glu Met Arg Leu
                85                  90                  95

Trp Ala Ile Val Ala Ser Glu Val Arg Leu Leu Leu Ser Thr Lys Trp
            100                 105                 110

Asn Val Gly Arg Leu Tyr Gln Leu Pro Ile Val Gly Ser Glu Glu Phe
        115                 120                 125

Ala Glu Tyr His Ser Gln Arg Glu Ala Leu Thr Asn Val Phe Arg Asp
    130                 135                 140

Leu Ala Thr Glu Ile Val Gly Asp Asp Pro Arg Ala Glu Leu Pro Phe
145                 150                 155                 160

His Ile Thr Met Ser Val Ile Glu Met Arg Arg Asn Asp Gly Lys Ile
                165                 170                 175

Pro Ser Pro Leu Ser Ala Asp Ser Leu Pro Glu Thr Ala Ile Met Leu
            180                 185                 190

Ala Asp Ala Ser Leu Ala Val Leu Gly Ala Pro Leu Pro Ala Asp Arg
        195                 200                 205

Val Glu Lys Thr Leu Glu Leu Ile Lys Gln Ala Asp Ala Lys
    210                 215                 220

<210> SEQ ID NO 8
<211> LENGTH: 2669
<212> TYPE: DNA
<213> ORGANISM: Corynebacterium glutamicum
<220> FEATURE:
<221> NAME/KEY: misc_feature
<222> LOCATION: (1)..(1000)
<223> OTHER INFORMATION: Sequence located upstream of the coding region
<220> FEATURE:
<221> NAME/KEY: CDS
<222> LOCATION: (1001)..(1666)
<223> OTHER INFORMATION: amtR allele
<220> FEATURE:
<221> NAME/KEY: mutation
<222> LOCATION: (1008)..(1008)
<223> OTHER INFORMATION: G > A transition
<220> FEATURE:
<221> NAME/KEY: misc_feature
<222> LOCATION: (1667)..(2669)
<223> OTHER INFORMATION: Sequence located downstream of the coding
    region

<400> SEQUENCE: 8
ctatgtctga ttctattggt gtcgcatgcg cagtgtagtt ttagaactac tagagaactg    60
gaaggaatca ctcgtgcttc acccctcatt gactgagcta gcggatgctg ccccacttgc   120
acaggatttt gccaccgtcc gcggtgtgct gaaggaatcg ctggatttgt tgggcaatgc   180

```
actgaaccac ggtgaagagc ccgcggagct tgcaggtgg ctgtcacaag ttattactga    240
tgttttgcac tccctggct tggatgccca cgtggtgctc accggcccg tggggcgtgg     300 agacgcactg cctacctcgc ccgtgaggtg gctggcggtc gtcgatagcc aagaagatcc   360
gaatgaaaag atttcagcgc tgttaactga ggtgggcttc attgcggagc cgatcggtgc   420
ggcaactcgt gaggagtggg agcagcgtgc gcgcgctggt gaggatccag aggtctattt   480
ggatgctggc acgtgggtcg cggcgatcgc tgaagtagat gacaaagcac tgttgcagga   540
tgcgttgtca tctaggccgc ctgcggtgga aacttatgag ggtcttcctt cgttggacat   600
ggtggtaaac attcgtgaga acctcatgat tcccacggtg aagatcgctc gctgggcagc   660
acacaaggct ggttctttgg cgcctacgac tgcgcagcgc ctcgtggatg cccgtggtgt   720
gctcaccaat gatgaagtcg acgcgctgac acaggtgtgg acttccgcac tgagcttgca   780
gtcgaaacgt tggatggatc acatccatga tcaagaaacc accgcttggg agcttcccgc   840
gctgcaacgt gccactttg gcgcatcggc tcggttgctt tctgaggtgt tgcggtccgt    900
tgaagcccgt gaaatcgata ccaaatagga actctgcaca attactggct acaatctctt   960
gagatcaata ggccaaactt taaggaagta gaattacgcg atg gca gaa gca gtg    1015
                                              Met Ala Glu Ala Val
                                              1               5 gga cgc ccc cgg aga tca gct ccg cga cgg gca ggc aag aat cct cgc    1063
Gly Arg Pro Arg Arg Ser Ala Pro Arg Arg Ala Gly Lys Asn Pro Arg
            10                  15                  20 gag gag att ctt gac gcc tct gct gag ctt ttc acc cgt caa ggc ttc    1111
Glu Glu Ile Leu Asp Ala Ser Ala Glu Leu Phe Thr Arg Gln Gly Phe
        25                  30                  35 gca aca acc tcc acg cat caa atc gct gat gcc gtg gga atc cgc caa    1159
Ala Thr Thr Ser Thr His Gln Ile Ala Asp Ala Val Gly Ile Arg Gln
    40                  45                  50 gcc tcg ctg tat tat cac ttc ccg tcc aag acg gaa atc ttc ctc acc    1207
Ala Ser Leu Tyr Tyr His Phe Pro Ser Lys Thr Glu Ile Phe Leu Thr
55                  60                  65 ctg ctg aaa tct act gtc gag ccg tcc act gtg ctc gcc gaa gac tta    1255
Leu Leu Lys Ser Thr Val Glu Pro Ser Thr Val Leu Ala Glu Asp Leu
70                  75                  80                  85 agc acc ctg gac gcc gga cct gag atg cgc ctc tgg gca atc gtt gcc    1303
Ser Thr Leu Asp Ala Gly Pro Glu Met Arg Leu Trp Ala Ile Val Ala
            90                  95                  100 tcc gaa gtg cgt ctg ctg ctg tcc acc aag tgg aac gtc ggt cgc ctg    1351
Ser Glu Val Arg Leu Leu Leu Ser Thr Lys Trp Asn Val Gly Arg Leu
        105                 110                 115 tac caa ctc ccc atc gtt ggt tct gaa gag ttc gcc gag tac cac agc    1399
Tyr Gln Leu Pro Ile Val Gly Ser Glu Glu Phe Ala Glu Tyr His Ser
    120                 125                 130 cag cgc gaa gcc ctc acc aac gtc ttc cgc gac ctc gcc acc gaa atc    1447
Gln Arg Glu Ala Leu Thr Asn Val Phe Arg Asp Leu Ala Thr Glu Ile
135                 140                 145 gtc ggt gac gac ccc cgc gca gaa ctc ccc ttc cac atc acc atg tcg    1495
Val Gly Asp Asp Pro Arg Ala Glu Leu Pro Phe His Ile Thr Met Ser
150                 155                 160                 165 gtg atc gaa atg cgt cgc aac gac ggc aag att cca agc ccg ctt tcc    1543
Val Ile Glu Met Arg Arg Asn Asp Gly Lys Ile Pro Ser Pro Leu Ser
            170                 175                 180 gca gac agc ctc ccg gag acc gca att atg ctt gcc gac gcc tcc ctc    1591
Ala Asp Ser Leu Pro Glu Thr Ala Ile Met Leu Ala Asp Ala Ser Leu
        185                 190                 195 gcc gtc ctc ggc gcg ccg ctg ccc gcc gac cgg gtc gaa aaa acg ctt    1639
```

```
              Ala Val Leu Gly Ala Pro Leu Pro Ala Asp Arg Val Glu Lys Thr Leu
                          200                 205                 210 gaa cta atc aag cag gct gac gcg aaa taaccatccg cgcctgcgaa              1686
Glu Leu Ile Lys Gln Ala Asp Ala Lys
            215                 220 atcaacggag catcaatcat ctgaccatcc agtttgaacg cacctggatg gtttttctgct     1746 tcctccacca ctttcttcgc ccactccaac tggttagcct ctggccgata ggctctccga      1806
acaatctcga tctgcttggg gtgaatgcat gcggtgccag cgaaaccagt ccgcgcagca      1866
tcgaccgctt ctaaatagag gccctcttca tcgtggaaat ccgcatggat ggcatcaatg      1926
gtgaacttcc cattcgccgc cgcgtggagg tgcatcaggg cgcgtgtaag cctcatggtg      1986
tctcggtagg agccttcatt ggactcatca cccaagaacc tagaatgagt gcctcccaag      2046
aggtgtgtga tcctccgc gccccagaac attccaacga ctttagggtc cgcagcaatc        2106
tgaggaatgc tggttgcagc ctgaggggtt tcaatcatgg cgataatgtt gaggccatct      2166
aattcctcag gcacgctgcc aagaagttta ggaaccataa caagtgtgaa atccgtggac      2226
ttcaccatct ccacgtcagc caaaaagtgt ggatcgctcg ccctacggt tctcacaatg       2286 gttcgtttag gatccaaccc cgattctcta atgttcctgt aggcgacctc acggtctacc      2346
tcccctgccc catcttccaa atcaatgatg accatatcgg ccttcgatgc tgcttttgga     2406
atgatctcag cacgtccagc tggtgcgaag agaaatagctg gtccacaaat aagttcagac     2466
atgtactcat taatacgcga aaaggcagac cttatggtct gccttcaagc gaaatcttta     2526
aaaactttag tgagcgaagt gtcgcgcacc agtcaggtac atggtcacgc cagccttgtt     2586
ggctgcctca atgacctcgt tgtcgcgaat ggatccacca ggctgcacaa cagcagtgat     2646
gccagcctca gcgagaacct caa                                             2669

<210> SEQ ID NO 9
<211> LENGTH: 222
<212> TYPE: PRT
<213> ORGANISM: Corynebacterium glutamicum

<400> SEQUENCE: 9

Met Ala Glu Ala Val Gly Arg Pro Arg Arg Ser Ala Pro Arg Arg Ala
1               5                   10                  15

Gly Lys Asn Pro Arg Glu Glu Ile Leu Asp Ala Ser Glu Leu Phe
            20                  25                  30

Thr Arg Gln Gly Phe Ala Thr Thr Ser Thr His Gln Ile Ala Asp Ala
        35                  40                  45

Val Gly Ile Arg Gln Ala Ser Leu Tyr Tyr His Phe Pro Ser Lys Thr
    50                  55                  60

Glu Ile Phe Leu Thr Leu Leu Lys Ser Thr Val Glu Pro Ser Thr Val
65                  70                  75                  80

Leu Ala Glu Asp Leu Ser Thr Leu Asp Ala Gly Pro Glu Met Arg Leu
                85                  90                  95

Trp Ala Ile Val Ala Ser Glu Val Arg Leu Leu Ser Thr Lys Trp
            100                 105                 110

Asn Val Gly Arg Leu Tyr Gln Leu Pro Ile Val Gly Ser Glu Glu Phe
        115                 120                 125

Ala Glu Tyr His Ser Gln Arg Glu Ala Leu Thr Asn Val Phe Arg Asp
    130                 135                 140

Leu Ala Thr Glu Ile Val Gly Asp Asp Pro Arg Ala Glu Leu Pro Phe
145                 150                 155                 160
```

```
His Ile Thr Met Ser Val Ile Glu Met Arg Arg Asn Asp Gly Lys Ile
            165                 170                 175

Pro Ser Pro Leu Ser Ala Asp Ser Leu Pro Glu Thr Ala Ile Met Leu
        180                 185                 190

Ala Asp Ala Ser Leu Ala Val Leu Gly Ala Pro Leu Pro Ala Asp Arg
            195                 200                 205

Val Glu Lys Thr Leu Glu Leu Ile Lys Gln Ala Asp Ala Lys
        210                 215                 220

<210> SEQ ID NO 10
<211> LENGTH: 672
<212> TYPE: DNA
<213> ORGANISM: Corynebacterium efficiens
<220> FEATURE:
<221> NAME/KEY: CDS
<222> LOCATION: (1)..(669)
<223> OTHER INFORMATION: amtR gene

<400> SEQUENCE: 10 atg gca ggt gca gtc gga cgc ccc cgg agg tca gct ccg cgt cgg gcg      48
Met Ala Gly Ala Val Gly Arg Pro Arg Arg Ser Ala Pro Arg Arg Ala
1               5                   10                  15 ggc aag aat ccc cgc gag gag att ctc gat gcc tca gct gag ctg ttc      96
Gly Lys Asn Pro Arg Glu Glu Ile Leu Asp Ala Ser Ala Glu Leu Phe
                20                  25                  30 acc cgc cag ggt ttc gcc acc acc tcc acg cac cag atc gcc gat gcc     144
Thr Arg Gln Gly Phe Ala Thr Thr Ser Thr His Gln Ile Ala Asp Ala
            35                  40                  45 gtg ggt atc cgg cag gcc tcc ctg tac tac cac ttc ccg tcc aag acg     192
Val Gly Ile Arg Gln Ala Ser Leu Tyr Tyr His Phe Pro Ser Lys Thr
        50                  55                  60 gag atc ttc ctc acc ctg ctg aaa tcc acc gtc gag cca tcc atg gtg     240
Glu Ile Phe Leu Thr Leu Leu Lys Ser Thr Val Glu Pro Ser Met Val
65                  70                  75                  80 ttg gcc ggc gac ctg gcc aat ctc gag gcc tcc ccg gag ctg cgc ctg     288
Leu Ala Gly Asp Leu Ala Asn Leu Glu Ala Ser Pro Glu Leu Arg Leu
                85                  90                  95 tgg gca ctg gtg gcg gcc gag gtg cgt cta ctg ctg tcg acg aag tgg     336
Trp Ala Leu Val Ala Ala Glu Val Arg Leu Leu Leu Ser Thr Lys Trp
            100                 105                 110 aat gtc ggt cgt ctc tat caa ctg ccg atc gtg gcc tcc gag gag ttc     384
Asn Val Gly Arg Leu Tyr Gln Leu Pro Ile Val Ala Ser Glu Glu Phe
        115                 120                 125 gag gag tac cac acg cag cgt gcc acc ctg acg gat acc ttc cgc agc     432
Glu Glu Tyr His Thr Gln Arg Ala Thr Leu Thr Asp Thr Phe Arg Ser
130                 135                 140 ctg gcc acg gag atc gtc ggt gag gat gac ccc cgt gcg gaa ctc ccg     480
Leu Ala Thr Glu Ile Val Gly Glu Asp Asp Pro Arg Ala Glu Leu Pro
145                 150                 155                 160 ttc cac atc acg atg tcc gcc atc gag atg cgc cgc aat gac ggc aag     528
Phe His Ile Thr Met Ser Ala Ile Glu Met Arg Arg Asn Asp Gly Lys
                165                 170                 175 gtt ccc agc ccc ctg tcg gag gac agc ctc ccg gac acc gcc gtc atg     576
Val Pro Ser Pro Leu Ser Glu Asp Ser Leu Pro Asp Thr Ala Val Met
            180                 185                 190 ctt gcc gac gcc gcc ctc gcc gtc ctg ggg gcc gac ctg ccc ggg gac     624
Leu Ala Asp Ala Ala Leu Ala Val Leu Gly Ala Asp Leu Pro Gly Asp
        195                 200                 205 cgg gtg gag cgc acc ctg gaa ctg ctc agg cag gct gac gcg aaa taa     672
Arg Val Glu Arg Thr Leu Glu Leu Leu Arg Gln Ala Asp Ala Lys
210                 215                 220
```

<210> SEQ ID NO 11
<211> LENGTH: 223
<212> TYPE: PRT
<213> ORGANISM: Corynebacterium efficiens

<400> SEQUENCE: 11

```
Met Ala Gly Ala Val Gly Arg Pro Arg Ser Ala Pro Arg Arg Ala
1               5                   10                  15

Gly Lys Asn Pro Arg Glu Glu Ile Leu Asp Ala Ser Ala Glu Leu Phe
            20                  25                  30

Thr Arg Gln Gly Phe Ala Thr Thr Ser Thr His Gln Ile Ala Asp Ala
        35                  40                  45

Val Gly Ile Arg Gln Ala Ser Leu Tyr Tyr His Phe Pro Ser Lys Thr
    50                  55                  60

Glu Ile Phe Leu Thr Leu Leu Lys Ser Thr Val Glu Pro Ser Met Val
65                  70                  75                  80

Leu Ala Gly Asp Leu Ala Asn Leu Glu Ala Ser Pro Glu Leu Arg Leu
                85                  90                  95

Trp Ala Leu Val Ala Ala Glu Val Arg Leu Leu Leu Ser Thr Lys Trp
            100                 105                 110

Asn Val Gly Arg Leu Tyr Gln Leu Pro Ile Val Ala Ser Glu Glu Phe
        115                 120                 125

Glu Glu Tyr His Thr Gln Arg Ala Thr Leu Thr Asp Thr Phe Arg Ser
    130                 135                 140

Leu Ala Thr Glu Ile Val Gly Glu Asp Pro Arg Ala Glu Leu Pro
145                 150                 155                 160

Phe His Ile Thr Met Ser Ala Ile Glu Met Arg Arg Asn Asp Gly Lys
                165                 170                 175

Val Pro Ser Pro Leu Ser Glu Asp Ser Leu Pro Asp Thr Ala Val Met
            180                 185                 190

Leu Ala Asp Ala Ala Leu Ala Val Leu Gly Ala Asp Leu Pro Gly Asp
        195                 200                 205

Arg Val Glu Arg Thr Leu Glu Leu Leu Arg Gln Ala Asp Ala Lys
    210                 215                 220
```

<210> SEQ ID NO 12
<211> LENGTH: 1266
<212> TYPE: DNA
<213> ORGANISM: Corynebacterium glutamicum
<220> FEATURE:
<221> NAME/KEY: CDS
<222> LOCATION: (1)..(1263)
<223> OTHER INFORMATION: lysC wild-type gene

<400> SEQUENCE: 12

```
atg gcc ctg gtc gta cag aaa tat ggc ggt tcc tcg ctt gag agt gcg      48
Met Ala Leu Val Val Gln Lys Tyr Gly Gly Ser Ser Leu Glu Ser Ala
1               5                   10                  15 gaa cgc att aga aac gtc gct gaa cgg atc gtt gcc acc aag aag gct      96
Glu Arg Ile Arg Asn Val Ala Glu Arg Ile Val Ala Thr Lys Lys Ala
            20                  25                  30 gga aat gat gtc gtg gtt gtc tgc tcc gca atg gga gac acc acg gat     144
Gly Asn Asp Val Val Val Val Cys Ser Ala Met Gly Asp Thr Thr Asp
        35                  40                  45 gaa ctt cta gaa ctt gca gcg gca gtg aat ccc gtt ccg cca gct cgt     192
Glu Leu Leu Glu Leu Ala Ala Ala Val Asn Pro Val Pro Pro Ala Arg
    50                  55                  60
```

-continued

```
gaa atg gat atg ctc ctg act gct ggt gag cgt att tct aac gct ctc         240
Glu Met Asp Met Leu Leu Thr Ala Gly Glu Arg Ile Ser Asn Ala Leu
 65                  70                  75                  80 gtc gcc atg gct att gag tcc ctt ggc gca gaa gcc caa tct ttc acg         288
Val Ala Met Ala Ile Glu Ser Leu Gly Ala Glu Ala Gln Ser Phe Thr
                 85                  90                  95 ggc tct cag gct ggt gtg ctc acc acc gag cgc cac gga aac gca cgc         336
Gly Ser Gln Ala Gly Val Leu Thr Thr Glu Arg His Gly Asn Ala Arg
            100                 105                 110 att gtt gat gtc act cca ggt cgt gtg cgt gaa gca ctc gat gag ggc         384
Ile Val Asp Val Thr Pro Gly Arg Val Arg Glu Ala Leu Asp Glu Gly
        115                 120                 125 aag atc tgc att gtt gct ggt ttc cag ggt gtt aat aaa gaa acc cgc         432
Lys Ile Cys Ile Val Ala Gly Phe Gln Gly Val Asn Lys Glu Thr Arg
    130                 135                 140 gat gtc acc acg ttg ggt cgt ggt ggt tct gac acc act gca gtt gcg         480
Asp Val Thr Thr Leu Gly Arg Gly Gly Ser Asp Thr Thr Ala Val Ala
145                 150                 155                 160 ttg gca gct gct ttg aac gct gat gtg tgt gag att tac tcg gac gtt         528
Leu Ala Ala Ala Leu Asn Ala Asp Val Cys Glu Ile Tyr Ser Asp Val
                165                 170                 175 gac ggt gtg tat acc gct gac ccg cgc atc gtt cct aat gca cag aag         576
Asp Gly Val Tyr Thr Ala Asp Pro Arg Ile Val Pro Asn Ala Gln Lys
            180                 185                 190 ctg gaa aag ctc agc ttc gaa gaa atg ctg gaa ctt gct gct gtt ggc         624
Leu Glu Lys Leu Ser Phe Glu Glu Met Leu Glu Leu Ala Ala Val Gly
        195                 200                 205 tcc aag att ttg gtg ctg cgc agt gtt gaa tac gct cgt gca ttc aat         672
Ser Lys Ile Leu Val Leu Arg Ser Val Glu Tyr Ala Arg Ala Phe Asn
    210                 215                 220 gtg cca ctt cgc gta cgc tcg tct tat agt aat gat ccc ggc act ttg         720
Val Pro Leu Arg Val Arg Ser Ser Tyr Ser Asn Asp Pro Gly Thr Leu
225                 230                 235                 240 att gcc ggc tct atg gag gat att cct gtg gaa gaa gca gtc ctt acc         768
Ile Ala Gly Ser Met Glu Asp Ile Pro Val Glu Glu Ala Val Leu Thr
                245                 250                 255 ggt gtc gca acc gac aag tcc gaa gcc aaa gta acc gtt ctg ggt att         816
Gly Val Ala Thr Asp Lys Ser Glu Ala Lys Val Thr Val Leu Gly Ile
            260                 265                 270 tcc gat aag cca ggc gag gct gcg aag gtt ttc cgt gcg ttg gct gat         864
Ser Asp Lys Pro Gly Glu Ala Ala Lys Val Phe Arg Ala Leu Ala Asp
        275                 280                 285 gca gaa atc aac att gac atg gtt ctg cag aac gtc tct tct gta gaa         912
Ala Glu Ile Asn Ile Asp Met Val Leu Gln Asn Val Ser Ser Val Glu
    290                 295                 300 gac ggc acc acc gac atc acc ttc acc tgc cct cgt tcc gac ggc cgc         960
Asp Gly Thr Thr Asp Ile Thr Phe Thr Cys Pro Arg Ser Asp Gly Arg
305                 310                 315                 320 cgc gcg atg gag atc ttg aag aag ctt cag gtt cag ggc aac tgg acc        1008
Arg Ala Met Glu Ile Leu Lys Lys Leu Gln Val Gln Gly Asn Trp Thr
                325                 330                 335 aat gtg ctt tac gac gac cag gtc ggc aaa gtc tcc ctc gtg ggt gct        1056
Asn Val Leu Tyr Asp Asp Gln Val Gly Lys Val Ser Leu Val Gly Ala
            340                 345                 350 ggc atg aag tct cac cca ggt gtt acc gca gag ttc atg gaa gct ctg        1104
Gly Met Lys Ser His Pro Gly Val Thr Ala Glu Phe Met Glu Ala Leu
        355                 360                 365 cgc gat gtc aac gtg aac atc gaa ttg att tcc acc tct gag att cgt        1152
Arg Asp Val Asn Val Asn Ile Glu Leu Ile Ser Thr Ser Glu Ile Arg
    370                 375                 380
```

```
att tcc gtg ctg atc cgt gaa gat gat ctg gat gct gct gca cgt gca       1200
Ile Ser Val Leu Ile Arg Glu Asp Asp Leu Asp Ala Ala Ala Arg Ala
385                 390                 395                 400 ttg cat gag cag ttc cag ctg ggc ggc gaa gac gaa gcc gtc gtt tat       1248
Leu His Glu Gln Phe Gln Leu Gly Gly Glu Asp Glu Ala Val Val Tyr
                405                 410                 415 gca ggc acc gga cgc taa                                                1266
Ala Gly Thr Gly Arg
            420

<210> SEQ ID NO 13
<211> LENGTH: 421
<212> TYPE: PRT
<213> ORGANISM: Corynebacterium glutamicum

<400> SEQUENCE: 13

Met Ala Leu Val Val Gln Lys Tyr Gly Gly Ser Ser Leu Glu Ser Ala
1               5                   10                  15

Glu Arg Ile Arg Asn Val Ala Glu Arg Ile Val Ala Thr Lys Lys Ala
            20                  25                  30

Gly Asn Asp Val Val Val Cys Ser Ala Met Gly Asp Thr Thr Asp
        35                  40                  45

Glu Leu Leu Glu Leu Ala Ala Ala Val Asn Pro Val Pro Pro Ala Arg
    50                  55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125

Lys Ile Cys Ile Val Ala Gly Phe Gln Gly Val Asn Lys Glu Thr Arg
    130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
        195                 200                 205

Ser Lys Ile Leu Val Leu Arg Ser Val Glu Tyr Ala Arg Ala Phe Asn
    210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Glu Ala Val Leu Thr
                245                 250                 255

Gly Val Ala Thr Asp Lys Ser Glu Ala Lys Val Thr Val Leu Gly Ile
            260                 265                 270

Ser Asp Lys Pro Gly Glu Ala Ala Lys Val Phe Arg Ala Leu Ala Asp
        275                 280                 285

Ala Glu Ile Asn Ile Asp Met Val Leu Gln Asn Val Ser Ser Val Glu
    290                 295                 300

Asp Gly Thr Thr Asp Ile Thr Phe Thr Cys Pro Arg Ser Asp Gly Arg
```

```
                305                 310                 315                 320
Arg Ala Met Glu Ile Leu Lys Lys Leu Gln Val Gln Gly Asn Trp Thr
                325                 330                 335

Asn Val Leu Tyr Asp Asp Gln Val Gly Lys Val Ser Leu Val Gly Ala
                340                 345                 350

Gly Met Lys Ser His Pro Gly Val Thr Ala Glu Phe Met Glu Ala Leu
                355                 360                 365

Arg Asp Val Asn Val Asn Ile Glu Leu Ile Ser Thr Ser Glu Ile Arg
    370                 375                 380

Ile Ser Val Leu Ile Arg Glu Asp Asp Leu Asp Ala Ala Arg Ala
385                 390                 395                 400

Leu His Glu Gln Phe Gln Leu Gly Gly Glu Asp Ala Val Val Tyr
                405                 410                 415

Ala Gly Thr Gly Arg
            420

<210> SEQ ID NO 14
<211> LENGTH: 28
<212> TYPE: DNA
<213> ORGANISM: Corynebacterium glutamicum
<220> FEATURE:
<223> OTHER INFORMATION: AmtR binding site upstream of the amtA gene

<400> SEQUENCE: 14
tttttaccta tcgttctata gatttctg                                            28

<210> SEQ ID NO 15
<211> LENGTH: 28
<212> TYPE: DNA
<213> ORGANISM: Corynebacterium glutamicum
<220> FEATURE:
<223> OTHER INFORMATION: AmtR binding site upstream of the amtA gene

<400> SEQUENCE: 15
gtattttcta ttccgctata gataaacc                                            28

<210> SEQ ID NO 16
<211> LENGTH: 28
<212> TYPE: DNA
<213> ORGANISM: Corynebacterium glutamicum
<220> FEATURE:
<223> OTHER INFORMATION: AmtR binding site upstream of the amtB gene

<400> SEQUENCE: 16
atattttcta tagtttaaca ggtaattt                                            28

<210> SEQ ID NO 17
<211> LENGTH: 28
<212> TYPE: DNA
<213> ORGANISM: Corynebacterium glutamicum
<220> FEATURE:
<223> OTHER INFORMATION: AmtR binding site upstream of the amtB gene

<400> SEQUENCE: 17
gctctaacta tagacctaca gaaactaa                                            28

<210> SEQ ID NO 18
<211> LENGTH: 28
<212> TYPE: DNA
<213> ORGANISM: Corynebacterium glutamicum
<220> FEATURE:
<223> OTHER INFORMATION: AmtR binding site upstream of the gltB gene
```

<400> SEQUENCE: 18
cgttttccta taggttgatc gaaagtaa                                              28

<210> SEQ ID NO 19
<211> LENGTH: 28
<212> TYPE: DNA
<213> ORGANISM: Corynebacterium glutamicum
<220> FEATURE:
<223> OTHER INFORMATION: AmtR binding site upstream of the gltB gene

<400> SEQUENCE: 19
ttattatcga acgattgata gaaacagg                                              28

<210> SEQ ID NO 20
<211> LENGTH: 669
<212> TYPE: DNA
<213> ORGANISM: Corynebacterium glutamicum
<220> FEATURE:
<223> OTHER INFORMATION: Corynebacterium glutamicum ATCC14067
<220> FEATURE:
<221> NAME/KEY: CDS
<222> LOCATION: (1)..(666)

<400> SEQUENCE: 20

```
atg gca gga gca gtg gga cgc ccc cgg aga tca gct ccg cga cgg gca        48
Met Ala Gly Ala Val Gly Arg Pro Arg Arg Ser Ala Pro Arg Arg Ala
1               5                   10                  15 ggc aag aat cct cgc gag gag att ctt gac gcc tct gct gag ctt ttc        96
Gly Lys Asn Pro Arg Glu Glu Ile Leu Asp Ala Ser Ala Glu Leu Phe
                20                  25                  30 acc cat caa ggc ttc gca aca acc tcc acg cat caa atc gct gat gcc       144
Thr His Gln Gly Phe Ala Thr Thr Ser Thr His Gln Ile Ala Asp Ala
            35                  40                  45 gtg gga atc cgc caa gcc tcg ctg tat tat cac ttc ccg tct aag acg       192
Val Gly Ile Arg Gln Ala Ser Leu Tyr Tyr His Phe Pro Ser Lys Thr
        50                  55                  60 gaa atc ttc ctc acc ctc ctg aaa tct acc gtc gag ccg tcc act gtg       240
Glu Ile Phe Leu Thr Leu Leu Lys Ser Thr Val Glu Pro Ser Thr Val
65                  70                  75                  80 ctc gcc gaa gac tta agc atc ctg gat gca gga cct gag atg cgc ctc       288
Leu Ala Glu Asp Leu Ser Ile Leu Asp Ala Gly Pro Glu Met Arg Leu
                85                  90                  95 tgg gca atc gtt gcc tcc gaa gtc cgt ctg ctg ctg tcc acc aag tgg       336
Trp Ala Ile Val Ala Ser Glu Val Arg Leu Leu Leu Ser Thr Lys Trp
                100                 105                 110 aac gtc ggt cgc ctg tac caa ctc ccc atc gtt ggt tct gaa gag ttc       384
Asn Val Gly Arg Leu Tyr Gln Leu Pro Ile Val Gly Ser Glu Glu Phe
            115                 120                 125 gcc gag tac cac agc cag cgc gaa gcc ctc acc aac gtc ttc cgc gac       432
Ala Glu Tyr His Ser Gln Arg Glu Ala Leu Thr Asn Val Phe Arg Asp
        130                 135                 140 ctc gcc acc gaa atc gtc ggt gac gac ccc cgc gca gaa ctc ccc ttc       480
Leu Ala Thr Glu Ile Val Gly Asp Asp Pro Arg Ala Glu Leu Pro Phe
145                 150                 155                 160 cac atc acc atg tcg gtg atc gaa atg cgt cgc aac gac ggc aag att       528
His Ile Thr Met Ser Val Ile Glu Met Arg Arg Asn Asp Gly Lys Ile
                165                 170                 175 cca agc ccg ctt tcc gca gac agc ctc ccg gag acc gca att atg ctt       576
Pro Ser Pro Leu Ser Ala Asp Ser Leu Pro Glu Thr Ala Ile Met Leu
            180                 185                 190 gcc gac gcc tcc ctc gcc gtc ctc ggc gcg tcg ctg ccc gcc gac cgg       624
Ala Asp Ala Ser Leu Ala Val Leu Gly Ala Ser Leu Pro Ala Asp Arg
```

```
                      195                 200                 205
gtc gaa aaa acg ctt gaa cta atc aag cag gct gac gcg aaa taa          669
Val Glu Lys Thr Leu Glu Leu Ile Lys Gln Ala Asp Ala Lys
    210                 215                 220
```

<210> SEQ ID NO 21
<211> LENGTH: 222
<212> TYPE: PRT
<213> ORGANISM: Corynebacterium glutamicum
<220> FEATURE:
<223> OTHER INFORMATION: Corynebacterium glutamicum ATCC14067

<400> SEQUENCE: 21

```
Met Ala Gly Ala Val Gly Arg Pro Arg Arg Ser Ala Pro Arg Arg Ala
1               5                   10                  15

Gly Lys Asn Pro Arg Glu Glu Ile Leu Asp Ala Ser Ala Glu Leu Phe
            20                  25                  30

Thr His Gln Gly Phe Ala Thr Thr Ser Thr His Gln Ile Ala Asp Ala
        35                  40                  45

Val Gly Ile Arg Gln Ala Ser Leu Tyr Tyr His Phe Pro Ser Lys Thr
    50                  55                  60

Glu Ile Phe Leu Thr Leu Leu Lys Ser Thr Val Glu Pro Ser Thr Val
65                  70                  75                  80

Leu Ala Glu Asp Leu Ser Ile Leu Asp Ala Gly Pro Glu Met Arg Leu
                85                  90                  95

Trp Ala Ile Val Ala Ser Glu Val Arg Leu Leu Leu Ser Thr Lys Trp
            100                 105                 110

Asn Val Gly Arg Leu Tyr Gln Leu Pro Ile Val Gly Ser Glu Glu Phe
        115                 120                 125

Ala Glu Tyr His Ser Gln Arg Glu Ala Leu Thr Asn Val Phe Arg Asp
    130                 135                 140

Leu Ala Thr Glu Ile Val Gly Asp Pro Arg Ala Glu Leu Pro Phe
145                 150                 155                 160

His Ile Thr Met Ser Val Ile Glu Met Arg Arg Asn Asp Gly Lys Ile
                165                 170                 175

Pro Ser Pro Leu Ser Ala Asp Ser Leu Pro Glu Thr Ala Ile Met Leu
            180                 185                 190

Ala Asp Ala Ser Leu Ala Val Leu Gly Ala Ser Leu Pro Ala Asp Arg
        195                 200                 205

Val Glu Lys Thr Leu Glu Leu Ile Lys Gln Ala Asp Ala Lys
    210                 215                 220
```

<210> SEQ ID NO 22
<211> LENGTH: 16
<212> TYPE: DNA
<213> ORGANISM: Corynebacterium glutamicum
<220> FEATURE:
<223> OTHER INFORMATION: Motif for AmtR regulator binding

<400> SEQUENCE: 22

```
atctatagaa cgatag                                                    16
```

<210> SEQ ID NO 23
<211> LENGTH: 16
<212> TYPE: DNA
<213> ORGANISM: Corynebacterium glutamicum
<220> FEATURE:
<223> OTHER INFORMATION: Motif for AmtR regulator binding

<400> SEQUENCE: 23

```
atctataggc ggatag                                                    16

<210> SEQ ID NO 24
<211> LENGTH: 23
<212> TYPE: PRT
<213> ORGANISM: Corynebacterium efficiens
<220> FEATURE:
<223> OTHER INFORMATION: AmtR Ceff

<400> SEQUENCE: 24

Leu Gly Ala Asp Leu Pro Gly Asp Arg Val Glu Arg Tyr Leu Glu Leu
1               5                   10                  15

Leu Arg Gln Ala Asp Ala Lys
            20

<210> SEQ ID NO 25
<211> LENGTH: 23
<212> TYPE: PRT
<213> ORGANISM: Corynebacterium efficiens
<220> FEATURE:
<223> OTHER INFORMATION: AmtR Cglu

<400> SEQUENCE: 25

Leu Gly Ala Pro Leu Pro Ala Asp Arg Val Glu Lys Tyr Leu Glu Leu
1               5                   10                  15

Ile Lys Gln Ala Asp Ala Lys
            20
```